US010285760B2

(12) United States Patent
Sadjadi et al.

(10) Patent No.: US 10,285,760 B2
(45) Date of Patent: May 14, 2019

(54) METHODS AND APPARATUS FOR IMPROVED ELECTROMAGNETIC TRACKING AND LOCALIZATION

(71) Applicant: Queen's University at Kingston, Kingston (CA)

(72) Inventors: Hossein Sadjadi, Kingston (CA); Elodie Lugez, Kingston (CA); Keyvan Hashtrudi-Zaad, Kingston (CA); Gabor Fichtinger, Kingston (CA)

(73) Assignee: Queen's University at Kingston, Kingston, Ontario (CA)

( * ) Notice: Subject to any disclaimer, the term of this patent is extended or adjusted under 35 U.S.C. 154(b) by 175 days.

(21) Appl. No.: 15/015,517

(22) Filed: Feb. 4, 2016

(65) Prior Publication Data

US 2016/0258782 A1    Sep. 8, 2016

Related U.S. Application Data

(60) Provisional application No. 62/111,836, filed on Feb. 4, 2015.

(51) Int. Cl.
*G01D 5/20* (2006.01)
*A61B 34/10* (2016.01)
(Continued)

(52) U.S. Cl.
CPC .............. *A61B 34/10* (2016.02); *A61B 34/20* (2016.02); *G01D 18/008* (2013.01); *A61B 34/30* (2016.02);
(Continued)

(58) Field of Classification Search
CPC ... A61B 34/10; A61B 34/20; A61B 2034/102; A61B 2034/107; A61B 2034/2051;
(Continued)

(56) References Cited

U.S. PATENT DOCUMENTS

| | | | |
|---|---|---|---|
| 5,930,741 | A | 7/1999 | Kramer |
| 6,335,617 | B1 | 1/2002 | Osadchy et al. |

(Continued)

FOREIGN PATENT DOCUMENTS

| | | |
|---|---|---|
| CA | 2120819 A1 | 4/1994 |
| CA | 2388328 C | 10/2000 |

(Continued)

OTHER PUBLICATIONS

Bender, H.-J., et al. "Reconstruction of 3D catheter paths from 2D X-ray projections." International Conference on Medical Image Computing and Computer-Assisted Intervention. Springer-Verlag Berlin Heidelberg, 1999: 981-989.

(Continued)

*Primary Examiner* — Dzung Tran
(74) *Attorney, Agent, or Firm* — Stephen J. Scribner

(57) ABSTRACT

An apparatus for electromagnetic (EM) tracking or localization is described which includes one or more EM transmitters and receivers (sensors, or trackers), an indication of relative locations of the one or more transmitter and sensor with respect to one or more instrument, optionally, a model of the one or more instrument flexibility, a measurement uncertainty analyzer that reports an uncertainty associated with each measurement, an equation of motion or dynamic model with motion constraints that describes an expected behavior of the one or more instrument, a probabilistic simultaneous localization and mapping (SLAM) algorithm that simultaneously estimates a pose of one or more instrument and updates a field distortion map, or parameters of a field distortion model, a field distortion estimator that uses currently-available information of the field distortion map and estimates field distortion in the vicinity of the one or more instrument, to be used for future measurement compensation, a transient analyzer that constantly observes (Continued)

variations in the field distortion map over time in order to differentiate regions with continuous changes from regions with constant field distortion, and provides feedback to the field distortion estimator, including indicating to what degree each region of the map is expected to change, wherein simultaneous field distortion mapping and electromagnetic tracking or localization of the one or more instrument is provided in real time.

13 Claims, 13 Drawing Sheets

(51) Int. Cl.
*A61B 34/20* (2016.01)
*G01D 18/00* (2006.01)
*A61B 17/34* (2006.01)
*A61B 34/30* (2016.01)

(52) U.S. Cl.
CPC . *A61B 2017/3413* (2013.01); *A61B 2034/102* (2016.02); *A61B 2034/107* (2016.02); *A61B 2034/2051* (2016.02); *A61B 2034/2055* (2016.02)

(58) Field of Classification Search
CPC ............ A61B 2034/2055; A61B 34/30; A61B 2017/3413; G01D 18/008
USPC .......................................................... 702/150
See application file for complete search history.

(56) References Cited

U.S. PATENT DOCUMENTS

| | | | |
|---|---|---|---|
| 6,553,326 B1 | 4/2003 | Kirsch et al. | |
| 7,373,271 B1 | 5/2008 | Schneider | |
| 7,508,195 B2 | 3/2009 | Anderson | |
| 7,912,662 B2 | 3/2011 | Zuhars et al. | |
| 8,040,127 B2 | 10/2011 | Jensen | |
| 8,131,342 B2 | 3/2012 | Anderson | |
| 8,228,028 B2 | 7/2012 | Schneider | |
| 8,326,402 B2 | 12/2012 | Bar-Tal et al. | |
| 8,354,837 B2 | 1/2013 | Anderson | |
| 8,391,952 B2 | 3/2013 | Anderson | |
| 8,536,859 B2 | 9/2013 | Bar-Tal et al. | |
| 2007/0016007 A1* | 1/2007 | Govari | A61B 5/0538 600/424 |
| 2007/0018649 A1* | 1/2007 | Prsha | G01V 3/088 324/326 |
| 2008/0079421 A1* | 4/2008 | Jensen | A61B 90/36 324/207.17 |
| 2009/0082665 A1* | 3/2009 | Anderson | A61B 5/06 600/424 |
| 2010/0117659 A1 | 7/2010 | Hethuin et al. | |
| 2013/0016185 A1* | 1/2013 | Stolka | A61B 1/041 348/46 |
| 2013/0216114 A1* | 8/2013 | Courtney | A61B 5/0066 382/130 |
| 2013/0218024 A1* | 8/2013 | Boctor | A61B 8/0841 600/476 |

FOREIGN PATENT DOCUMENTS

| | | |
|---|---|---|
| CA | 2761547 A1 | 12/2011 |
| CA | 2762262 A1 | 12/2011 |
| EP | 1153292 B1 | 12/1999 |
| EP | 1421900 B1 | 11/2003 |
| WO | WO2001/063312 A1 | 2/2001 |
| WO | WO2004/091391 A1 | 4/2004 |
| WO | WO2007/069186 A2 | 12/2006 |
| WO | WO2007/113719 A1 | 10/2007 |
| WO | WO2010/076676 A1 | 11/2009 |
| WO | WO2013/088278 A1 | 11/2012 |

OTHER PUBLICATIONS

Zhou, Jun, et al. "Real-time catheter tracking for high-dose rate prostate brachytherapy using an electromagnetic 3D-guidance device: A prelininary performance study." Medica Physucs 40.2 (2013): 021716-1-8.

Bharat, Shyam, et al. "Electromagnetic tracking for catheter reconstruction in ultrasound-guided high-dose-rate brachytherapy of the prostate." Brachytherapy 13.6 (2014): 640-650.

Poulin, Eric, et al, "Fast, automatic, and accurate catheter reconstruction in HDR brachytherapy using an electromagnetic 3D tracking system." Medical Physics 42.3 (2015): 1227-1232.

* cited by examiner

METHODS AND APPARATUS FOR IMPROVED ELECTROMAGNETIC TRACKING AND LOCALIZATION

RELATED APPLICATION

This application claims the benefit of the filing date of U.S. application Ser. No. 62/111,836, filed on Feb. 4, 2015, the contents of which are incorporated herein by reference in their entirety.

BACKGROUND

Localization and tracking of medical instruments is an integral part of computer-assisted interventions and several technologies have been introduced for this purpose. Depending on the underlying working principles, each technology imposes some limitation on the usability of the tracking system. For example, electromagnetic (EM) tracking technology, in which known local EM fields are generated by transmitters in order to localize EM sensors (trackers) placed within the field, using the principle of mutual induction, has been integrated into various commercial products, and applied in several interventions. This popularity is primarily due to freedom from line-of-sight restrictions, small sensor size, and the ability to track instruments inside the patient's body, which is particularly helpful for guiding needles, catheters, and guide-wires, during insertions or placements.

However, EM trackers are highly susceptible to distortions caused by magnetic or electrically-conductive objects located in the close proximity of the tracking volume. In a clinical environment, such sources of field distortion include medical imaging devices (C-arm, CT gantry, etc.), equipment (tables, monitors, etc.), and instruments. The interference causes tracking errors ranging from a few millimeters in research environments to a few centimeters in clinical environments, especially in the presence of certain equipment, such as a C-arm fluoroscopy, known to significantly distort the EM field while unavoidable in many procedures.

Unless compensated for, the tracking error due to field distortion compromises the outcome of medical procedures and limits the reliability and utility of EM tracking in clinical settings. If this limitation is alleviated, EM tracking technology can open its way into new potential clinical procedures currently not possible. Current approaches used to reduce the impact of field distortion can be classified into three categories: reduction, detection, and compensation.
1) Reduction: These methods can help reduce the amount of field distortion caused by field distorting objects. For existing EM tracking systems, these methods may include object shielding, EM field type modification (e.g., from AC to pulsed-DC), or optimum positioning (patient, devices, and EM transmitter).
2) Detection: These techniques can help detect or monitor the amount of field distortion, or confirm if a tool can be tracked using EM trackers. They mostly rely on measurements of the induced currents in various (and normally redundant) coils or sensors. For example, a redundant EM sensor is placed at a known fixed location with respect to another sensor or the transmitter, and the variations of the measured location of the redundant sensor compared to its known fixed location are used to detect or monitor the amount of field distortion.
3) Compensation: These methods can help compensate for the field distortion and can further be classified into two sub-categories: static pre-calibration, and fusion.
   i. Static pre-calibration is useful in environments where field distorting objects are stationary and the amount of distortion at each point in the tracking volume is invariable. In this case, a distortion map can be generally created pre-operatively in order to establish a relationship between each point in the workspace and the corresponding magnitude of distortion at that point. The created distortion map can be stored in various forms such as look-up tables, polynomial fitting, interpolation, or neural networks, or other methods. This map can subsequently be used intra-operatively to compensate for the undesired static distortion.
   ii. Fusion approaches rely on redundant and independent (undistorted) measurements, such as alternative types of tracking systems (optical, imaging, inertial, etc.) or an array of EM transmitters and/or sensors fixed at known spatial coordinates. The distortion map is then created based on fusion of the information provided by the alternative tracker, or the assumption that the sensor array remains partially undistorted. This map can subsequently be used to compensate for field distortion.

While the currently available methods for field distortion compensation may offer improved tracking performance, they as well impose severe constraints and incorporate substantial underlying limitations. Reduction and detection methods may be able to minimize the error due to a specific field distorting tool. However, these techniques generally lack the ability to compensate for the errors in the entire workspace or due to multiple field distorting objects. Static pre-calibration is a time consuming procedure as the sensor must be positioned at numerous points in the workspace. It also requires ground truth measurements by means of manual positioning, calibration phantom, robotic arm, or other tracking devices. Even after such a lengthy and tedious calibration procedure, the map is valid only for a static environment. Therefore, this method is unable to cope with the dynamic nature of most clinical settings. As a result, during the clinical procedure, this resource intensive calibration process should be repeated for every field distortion change, and a critical portion of the workspace where the patient is positioned may be inaccessible during such consequent recalibrations. Overall, in true clinical settings with dynamic changes due to movement or operation of imaging devices, surgical tools, tables, monitors, etc., this approach is ineffective and may in fact exacerbate the tracking error if the distortion map is outdated. Fusion-based methods are inefficient in nature as they either demand external tracking technologies, or an unnecessarily large number of redundant elements, in which case the field distortion is also determined accurately only in the vicinity of the redundant elements mounted typically on the exterior surface of the workspace and away from the region of interest. Furthermore, these methods are costly, may introduce additional errors due to spatial/temporal calibration between the tracking systems or sensors, and overcrowd the surgical site with excessive devices.

Accordingly, there is a need for effective detection and compensation for field distortion error.

SUMMARY

Described herein is an apparatus for electromagnetic (EM) tracking or localization, comprising: one or more EM transmitters and receivers (sensors, or trackers); an indication of relative locations of the one or more transmitter and sensor with respect to one or more instrument; optionally, a model of the one or more instrument flexibility; a measurement uncertainty analyzer that reports an uncertainty associated with each measurement; an equation of motion or dynamic model with motion constraints that describes an expected behavior of the one or more instrument; a probabilistic simultaneous localization and mapping (SLAM) algorithm that simultaneously estimates a pose of one or more instrument and updates a field distortion map, or parameters of a field distortion model; a field distortion estimator that uses currently-available information of the field distortion map and estimates field distortion in the vicinity of the one or more instrument, to be used for future measurement compensation; a transient analyzer that constantly observes variations in the field distortion map over time in order to differentiate regions with continuous changes from regions with constant field distortion, and provides feedback to the field distortion estimator, including indicating to what degree each region of the map is expected to change; wherein simultaneous field distortion mapping and electromagnetic tracking or localization of the one or more instrument is provided in real time.

Also described herein is a method for electromagnetic (EM) tracking or localization, comprising: providing, as input to a probabilistic SLAM algorithm: an indication of relative locations of one or more transmitter and sensor with respect to one or more instruments; optionally, a model of the one or more instrument flexibility; an uncertainty associated with each measurement; and an expected behavior of the one or more instrument, using an equation of motion or dynamic model with motion constraints; using the SLAM algorithm to simultaneously estimate a pose of the one or more instrument and update a field distortion map, or parameters of a field distortion model; estimating field distortion using currently-available information of the field distortion map and estimating field distortion in the vicinity of the one or more instrument, and using the estimates for future measurement compensation; and continuously observing variations in the field distortion map over time to differentiate regions with continuous changes from regions with constant field distortion, and providing feedback to a field distortion estimator, including indicating to what degree each region of the map is expected to change; wherein simultaneous field distortion mapping and electromagnetic tracking or localization of the one or more instrument is provided in real time.

In one embodiment the field distortion estimator estimates field distortion based on interpolating, or adjusting model parameters of the field distortion map.

In one embodiment the SLAM algorithm uses Bayesian inference for estimation and is implemented by one or more of a Kalman filter, a particle filter, and non-linear least squares.

Also described herein is programmed media for use with a computer and with data such as, for example, estimates of the pose of one or more instrument, a field distortion map, parameters of a field distortion model, the programmed media comprising a computer program stored on non-transitory storage media compatible with the computer, the computer program containing instructions to direct the computer to perform one or more of the functions described in herein, and provide an output of the tracking or localization of the one or more instrument in real time.

Also described herein is an apparatus for electromagnetic (EM) tracking or localization, comprising: one or more EM transmitters and receivers (sensors, or trackers); a processor that receives and/or processes one or more of: an indication of relative locations of the one or more transmitter and sensor with respect to one or more instrument; optionally, a model of the one or more instrument flexibility; optionally, a measurement uncertainty analyzer that reports an uncertainty associated with each measurement; optionally, a field distortion compensation technique; an equation of motion or dynamic model with motion constraints, such as a non-holonormic constraint, that describes an expected behavior of the one or more instrument; wherein the processor outputs a result Wherein the one or more instrument is localized or reconstructed in in real-time or off-line.

In one embodiment measurements are combined or filtered with kinematic motion models and/or dynamic motion models, including but not limited to weighted averages, or a stochastic sensor fusion technique. One embodiment includes a Kalman filter.

Also described herein is method for electromagnetic (EM) tracking or localization, comprising: providing, as input to a processor that includes a filtering algorithm: an indication of relative locations of one or more transmitter and sensor with respect to one or more instrument; optionally, a model of the one or more instrument flexibility; a motion model with constraints that describe an expected behavior of each of the one or more instrument; analyzing a measurement uncertainty and reporting an uncertainty associated with each measurement; optionally applying a field distortion compensation technique; using the filtering algorithm to reconstruct and/or localize the one or more instrument path; wherein the one or more instrument path is tracked, localized, or reconstructed in in real-time or off-line.

In one embodiment the method comprises combining or filtering measurements with a kinematic motion model and/or a dynamic motion model.

In one embodiment the method comprises a weighted average technique or a stochastic sensor fusion technique.

In one embodiment the the filtering algorithm comprises a Kalman filter.

Also described herein is programmed media for use with a computer and with data such as, for example, an indication of relative locations of one or more transmitter and sensor with respect to one or more instrument; optionally, a model of the one or more instrument flexibility; a motion model with constraints that describe an expected behavior of each of the one or more instrument; the programmed media comprising a computer program stored on non-transitory storage media compatible with the computer, the computer program containing instructions to direct the computer to perform one or more of the functions described in claim 11, and provide an output of the tracking or localization of the one or more instrument path in real time.

In various embodiments, the instrument may be an object or feature being tracked or localized; wherein the instrument comprises a gaming device, a tool, a surgical tool (such as a catheter, a needle, a cutting or cautery tool, a guide-wire), an animal or a human, or a feature in a simulator.

BRIEF DESCRIPTION OF THE DRAWINGS

For a better understanding of the invention and to show more clearly how it may be carried into effect, reference will now be made, by way of example, to the accompanying drawings, wherein.

DETAILED DESCRIPTION OF EMBODIMENTS

Figure 1A:
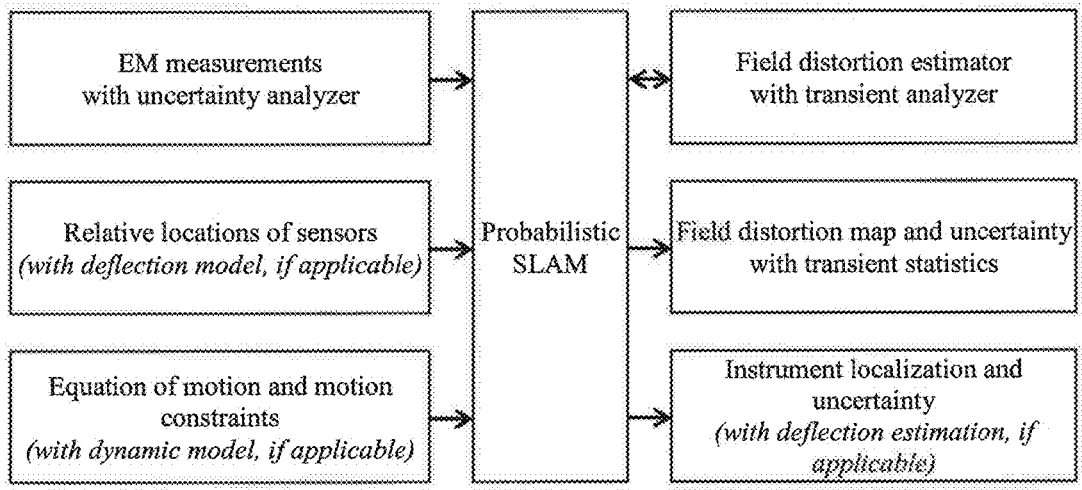
FIGS. 1A, 1B, and 1C show generalized workflow diagrams according to various embodiments.

Methods and apparatus described herein eliminate or minimize the above-described drawbacks of currently-available electromagnetic tracking systems.

Presented herein are apparatus, methods, and constructs for improving EM tracking and localization. Some embodiments provide dynamic EM field distortion compensation. Embodiments may be used to track and/or localize an instrument. Some embodiments integrate a tracked instrument's equation of motion (or/and its dynamic model) including motion constraints with EM tracker observations, and apply a simultaneous localization and mapping (SLAM) algorithm to both accurately estimate the pose of the instrument and create a map for the field distortion in real-time. Such embodiments may rely on redundant elements (sensors or transmitters) fixed on a rigid or flexible instrument, in which case the instrument's flexibility can as well be modeled and incorporated into the SLAM algorithm. In the case of flexible instruments, such as needles, catheters, tubes, etc., the SLAM algorithm not only estimates the pose of the instrument along with the field distortion map, but it also estimates the instrument deflection in real-time. Example 1, below, is an embodiment designed for surgical applications, although the invention is not limited thereto.

Other embodiments provide path localization using EM tracking technology. Embodiments may be used to track and/or localize an instrument. Some embodiments comprise a filtering technique that incorporates nonholonomic motion constraints of an EM sensor (or redundant sensors) in an instrument path, to reduce EM tracking error. In contrast to conventional filtering techniques that rely only on position measurements, embodiments described herein use both position and orientation measurements as well as the nonholonomic motion constraint, in order to accurately reconstruct an instrument path. For example, one embodiment may include Kalman filters to integrate both the position and orientation EM measurements with the nonholonomic motion constraints of the sensor along the instrument path. Examples 2 and 3, below, are embodiments for catheter path reconstruction, and Example 4 is an embodiment for tracking an ultrasound probe, although the invention is not limited thereto.

As used herein, the term "instrument" is intended to refer to an object or feature being tracked or localized in a given application. As non-limiting examples, the term "instrument" may refer to an object such as a gaming device, a tool, a surgical tool (such as a catheter, a needle, a cutting or cautery tool, a guide-wire), an animal or a human, or a feature in a simulator.

As described herein, certain embodiments of the invention integrate a tracked instrument's equation of motion (or/and its dynamic model) including motion constraints with EM tracker observations, and apply a simultaneous localization and mapping algorithm to both accurately estimate the pose of the instrument and create a map for the field distortion in real-time. The method may rely on redundant elements (sensors or transmitters) fixed on a rigid or flexible instrument, in which case the instrument's flexibility can as well be modeled and incorporated into the SLAM algorithm. In the case of flexible instruments, such as needles, catheters, tubes, etc., the SLAM algorithm not only estimates the pose of the instrument along with the field distortion map, but it also estimates the instrument deflection in real-time.

A feature of certain embodiments described herein is the provision of real-time robust tracking of an instrument, using significantly fewer redundant elements than used in prior approaches to reduce field distortion. Moreover, the field distortion is directly determined for the point at which the instrument is located, rather than on the boundary or the surface of the workspace, leading to a more precise pose estimation of the tracked instruments. Embodiments described herein are particularly desirable for EM tracking used in medical applications; however, the formulation is general and applicable to other applications, such as, but not limited to, virtual reality systems, navigation systems, manipulators, and simulators.

Embodiments may be customized for particular applications.

Some embodiments may include hardware and/or software components selected from the following:

One or more EM transmitters and receivers (i.e., sensors, or trackers).

A processor (e.g., a computer) that receives and/or processes and/or performs one or more function as described below, and outputs tracking and/or localization of one or more instrument.

Relative locations of the transmitters and sensors with respect to the instrument, as well as a model of the instrument flexibility (if required).

Measurement uncertainty analyzer that reports the uncertainty associated with each measurement. This information may be provided by a tracking system manufacturer (as a quality measure) or inferred from factors such as, for example, the known fixed position of redundant elements, the known fixed orientation of sensors or sensor elements (e.g., coils inside the sensors), measurement variations over a fixed time interval, etc.

Equation of motion (or dynamic model) with motion constraints to describe an expected behavior of the instrument.

A probabilistic SLAM algorithm that simultaneously estimates the pose of one or more tracked instruments and updates a field distortion map, or parameters of the field distortion model. The algorithm may use Bayesian inference for estimation and may be implemented by one or more of Kalman filters, particle filters, non-linear least squares, etc., but is not limited thereto.

Field distortion estimator that uses currently available information of the map and estimates field distortion in the vicinity of the instrument, to be used for future measurement, compensation. This may be based on interpolating, or adjusting model parameters of a field distortion map.

Transient analyzer that constantly observes variations in the field distortion map over time in order to differentiate regions with continuous changes from regions with constant field distortion, and provide feedback to the field distortion estimator, including indicating to what degree each region of the map is expected to change. For example, field distortion may be more varying where small tools are moved in the workspace, while it may be less varying where an imaging device such as a fluoroscope is located.

An output comprising a result wherein the one or more instrument is localized or tracked in in real-time or off-line.

Figure 1B:
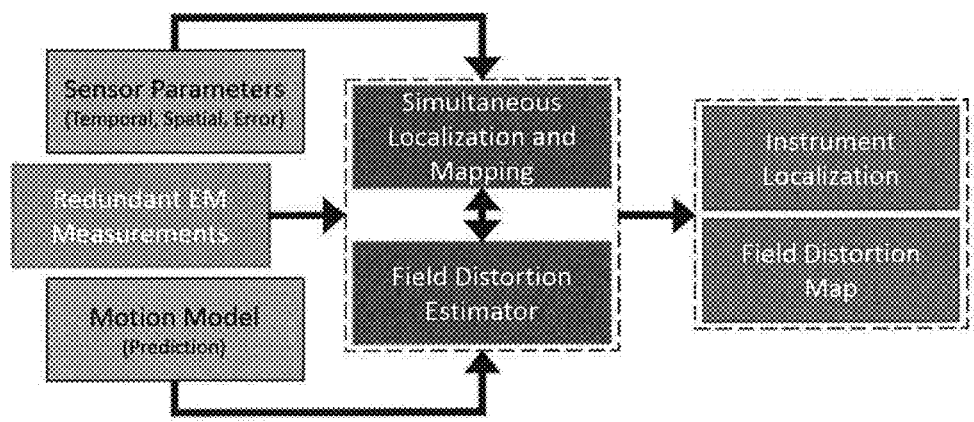
Figure 1C:
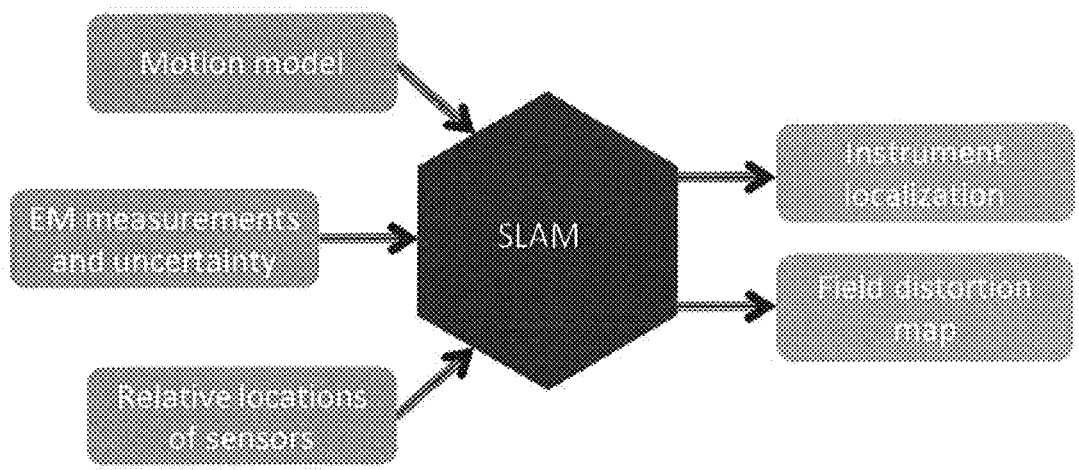

Embodiments may comprise a workflow generally illustrated in FIG. 1A, 1B, or 1C, or a combination thereof.

Embodiments may include programmed media for use with a computer and with data such as, for example, estimates the pose of one or more tracked instruments, a field distortion map, parameters of a field distortion model, the programmed media comprising a computer program stored on non-transitory storage media compatible with the computer, the computer program containing instructions to direct the computer to perform one or more of the functions described above and/or in FIG. 1A, 1B, or 1C, or a combination thereof.

By incorporating a dynamic model and an equation of motion together with a SLAM algorithm for field distortion compensation, embodiments eliminate the need for the fusion of other tracking technologies and avoid use of a large number of redundant EM transmitters/sensors. Further, use of a field distortion transient analyzer may significantly improve performance of the field distortion estimator.

Some embodiments may include hardware and/or software components selected from the following:

One or more EM transmitters and receivers (sensors, or trackers);

A processor (e.g., a computer) that receives and/or processes and/or performs one or more function as described below; and outputs tracking and/or localization of one or more instrument.

An indication of relative locations of the one or more transmitter and sensor with respect to the one or more instrument.

Optionally, a model of the one or more instrument flexibility.

Optionally, a measurement uncertainty analyzer that reports an uncertainty associated with each measurement.

Optionally, a field distortion compensation technique.

An equation of motion or dynamic model with motion constraints, such as a nonholonomic constraint, that describes an expected behavior of the one or more instrument.

Combining or filtering measurements with kinematic motion models and/or dynamic motion models; including but not limited to weighted averages, or a stochastic sensor fusion technique, or a Kahnan filter.

An output comprising a result wherein the one or more instrument is localized or reconstructed in in real-time or off-line.

Embodiments may include programmed media for use with a computer and with data such as, for example, an indication of relative locations of one or more transmitter and sensor with respect to one or more instrument; optionally, a model of the one or more instrument flexibility; a motion model with constraints that describe an expected behavior of each of the one or more instrument; the programmed media comprising a computer program stored on non-transitory storage media compatible with the computer, the computer program containing instructions to direct the computer to perform one or more of the functions described herein, and provide an output of the tracking or localization of the one or more instrument path in real time.

Embodiments may include a data processing system that controls one or more components of the system, e.g., one or more components such as those shown in FIGS. 1A, 1B, and 1C, in conjunction with a user interface (e.g., a graphical user interface (GUI)). Controlling may include functions such as receiving input (image data such as ultrasound data, commands from a user of the system, etc.), analyzing data, and displaying results and/or images on a display of the system.

The data processing system may be a client and/or server in a client/server system. For example, the data processing system may be a server system or a personal computer (PC) or tablet-based system. The data processing system may include an input device, a central processing unit (CPU), memory, display device, and interface device. The input device may include a keyboard, a mouse, a trackball, a touch sensitive surface or screen, or a similar device. The display may include a computer screen, television screen, display screen, terminal device, a touch sensitive display surface or screen, or a hardcopy producing output device such as a printer or plotter. The memory may include a variety of storage devices including internal memory and external mass storage typically arranged in a hierarchy of storage as understood by those skilled in the art. For example, the memory may include databases, random access memory (RAM), read-only memory (ROM), flash memory, and/or disk devices. The interface device may include one or more network connections. The data processing system may be adapted for communicating with other data processing systems over a network via the interface device. For example, the interface device may include an interface to a network such as the Internet and/or another wired or wireless network (e.g., a wireless local area network (WLAN), a cellular telephone network, etc.). Thus, the data processing system may be linked to other data processing systems by the network. The CPU may include or be operatively coupled to dedicated coprocessors, memory devices, or other hardware modules. The CPU is operatively coupled to the memory which stores an operating system for general management of the system. The CPU is operatively coupled to the input device for receiving user commands or queries and for displaying the results of these commands or queries to the user on the display. Commands and queries may also be received via the interface device and results may be transmitted via the interface device. The data processing system may include a database system (or storage) for storing data and programming information. The database system may include a database management system and a database and may be stored in the memory of the data processing system. In general, the data processing system has stored therein data representing sequences of instructions which when executed cause certain steps of the method described herein to be performed. For example, the instructions may be associated with one or more components of FIGS. 1A, 1B, or 1C. Of course, the data processing system may contain additional software and hardware, a description of which is not necessary for understanding the invention.

Thus, the data processing system includes computer executable programmed instructions for directing the system to implement the embodiments of the invention. Executing instructions may include the system prompting the user for input at various steps, some of which are shown in the embodiments of FIGS. 1A, 1B, and 1C. In one embodiment the programmed instructions may be embodied in one or more hardware modules or software modules resident in the memory of the data processing system or elsewhere. In one embodiment the programmed instructions may be embodied on a non-transitory computer readable storage medium or product (e.g., a compact disk (CD), etc.) which may be used for transporting the programmed instructions to the memory of the data processing system and/or for executing the programmed instructions. In one embodiment the programmed instructions may be embedded in a computer-readable signal or signal-bearing medium (or product) that is uploaded to a network by a vendor or supplier of the programmed instructions, and this signal or signal-bearing medium may be downloaded through an interface to the data processing system from the network by end users or potential buyers.

A user may interact with the data processing system and its hardware and software modules using a GUI. The GUI may be used for controlling, monitoring, managing, and accessing the data processing system. GUIs are supported by common operating systems and provide a display format which enables a user to choose commands, execute application programs, manage computer files, and perform other functions by selecting pictorial representations known as icons, or items from a menu through use of an input device such as a mouse or touch screen. In general, a GUI is used to convey information to and receive commands from users and generally includes a variety of GUI objects or controls, including icons, toolbars, drop-down menus, text, dialog boxes, buttons, and the like. A user typically interacts with a GUI presented on a display by using an input device (e.g., a mouse or touchscreen) to position a pointer or cursor over an object (e.g., an icon) and by "clicking" on the object. Typically, a GUI based system presents application, system status, and other information to the user in one or more "windows" appearing on the display. A window is a more or less rectangular area within the display in which a user may view an application or a document. Such a window may be open, closed, displayed full screen, reduced to an icon, increased or reduced in size, or moved to different areas of the display. Multiple windows may be displayed simultaneously, such as: windows included within other windows, windows overlapping other windows, or windows tiled within the display area.

Embodiments will be further described by way of the following non-limiting Examples.

EXAMPLE 1

Simultaneous Electromagnetic Tracking and Calibration for Dynamic Field Distortion Compensation Localization and tracking of medical instruments is fundamental in computer-assisted interventions. The tracking can be performed using electromagnetic (EM) tracking systems, in which known local EM fields are generated by transmitters in order to localize EM sensors (trackers) placed within the field, using the principle of mutual induction. EM trackers are highly susceptible to distortions caused by magnetic or electrically-conductive objects located in the close proximity of the tracking volume. In a clinical environment, such sources of field distortion include medical imaging devices (C-arm, CT gantry, etc.), equipment (tables, monitors, etc.), and instruments. The interference causes measurement bias and results in tracking errors ranging from a few millimeters in research environments to a few centimeters in clinical environments. Unless compensated for, this error compromises the outcome of medical procedures and limits the reliability and utility of EM tracking in clinical settings.

Existing approaches employed to compensate for the field distortion mainly rely on static pre-calibration or fusion. Pre-calibration involves a tedious procedure in which the entire workspace is scanned and a distortion map is created pre-operatively. However, this map is valid for only static environments and cannot cope with the dynamic nature of most clinical settings. To address this limitation, fusion-based approaches make use of redundant and independent (undistorted) means of measurement, such as optical trackers, or an array of EM sensors to dynamically map and compensate for field distortion. These methods are inefficient as they demand external tracking technologies, or an unnecessarily large number of EM sensors. As a result, various clinical applications of EM tracking technology are still hampered by limitations caused due to field distortion.

This example describes a method to dynamically map field distortion and effectively compensate for the tracking error. To alleviate the limitations of the existing approaches, redundant EM sensors are used to dynamically map and compensate for field distortion. Specifically, motion models of tracked instruments are integrated, including motion constraints, with EM sensor observations, and a simultaneous localization and mapping (SLAM) algorithm (Durrant-Whyte, H., et al., Robotics & Automation Magazine, 13:99-110, 2006) is applied. The SLAM technique has proven to be successful in various mobile robotics applications, where the knowledge of motion models, measurements, and uncertainties can be combined to provide statistically reliable estimates.

Using several (e.g., 1 to 3) redundant sensors mounted on the tracked instrument, the method provides real-time field distortion mapping, similar to the dynamic sensor array fusion, but with significantly fewer redundant elements than prior approaches to estimate the pose of the instrument and create a map for the field distortion in real-time. Furthermore, as the redundant elements are placed on the instrument, the field distortion is directly estimated for the point at which the instrument is located, rather than at discrete locations of the sensor array elements mounted on the exterior surface of the workspace. This leads to a more precise pose estimation. The method is particularly desirable for EM tracking technology employed in medical applications; however, the formulation is generic and applicable to other fields such as virtual reality systems, simulation platforms, and navigation systems.

Electromagnetic Tracking Error

Numerous sources can contribute to the overall tracking error. The sources may be broadly classified into internal (inherent), and external (environmental) errors.

Internal sources of error may include limitations in design (e.g., simplified laws of physics, algorithmic singularities) or limitations in implementation (e.g., amplified thermal activity, variations in timing). These errors are normally handled at the manufacturer level, minimized via factory calibrations, and detailed in system specifications.

External sources are mainly due to background magnetic field distortion (environmental noise) interfering with the tracking device. This is caused by magnetic or electrically-conductive objects located within close proximity of the tracking volume, such as medical imaging devices, equipment, and instruments. These errors are significantly higher than internal errors, and they may be reduced at the operator level with variations in the operating environment or experimental design.

The amount of error depends considerably on whether the workspace is static or dynamic. A static condition describes the situation of localizing a stationary target, while there are no changes in the environment. In contrast, a dynamic condition refers to the situation of tracking a moving target while there may also be changes in the operating environment.

The resulting tracking error is normally characterized as random error, or systematic error. Random errors appear as noise or jitter in measurements and can be reduced with signal processing. Systematic errors, however, appear as offset or bias in measurements and are more difficult to compensate. In particular, field distortion (external and predominantly dynamic) is the leading cause of systematic error, which significantly limits the utility of EM trackers in clinical settings.

Various methods have been proposed to overcome the tracking challenges posed by EM field distortion. These methods can be classified into three categories: detection, reduction, and compensation, as described above. However, there is still a need for methods that can dynamically map field distortions and effectively compensate for the tracking error.

Materials and Methods

This method achieves dynamic field distortion compensation in two steps. First, a system identification step is performed to identify the relative coordinates and properties of the redundant EM sensors mounted on the tracked instrument. Second, a simultaneous tracking and calibration step is performed to compensate for field distortion in real-time, A. System Identification This step is only required if the parameters of the experimental setup are not previously known. In this case, the system identification is performed only once and off-line (pre-operatively) in a controlled environment free from field distorting objects. The system identification is independent of the SLAM process (the next step) and the actual operating environment. The objective is to quantify spatial, temporal, and error parameters of the sensors.

1) Spatial Parameters

Given a total of n EM sensors mounted rigidly on a tracked target, the spatial (kinematic) parameters identify the relative transformations between the sensor frames $\{S_i\}$, (i=1, 2, . . . , n) and an arbitrary tracked frame $\{P\}$ on the target. As an example, a conceptual diagram has been developed where redundant EM sensors are used to track the target frame $\{P\}$. Here, the transformations $T_{Ref}^{S_i}$ from each sensor frame $\{S_i\}$ to the EM tracker reference frame $\{Ref\}$ are provided by the EM tracking system, and the transformations $T_{S_i}^{P}$ from $\{P\}$ to each sensor $\{S_i\}$ should be computed.

To generalize this example, suppose an independent tracking system, such as an optical tracker is also used to provide ground truth observations of the frame $\{P\}$. These independent observations are not part of the method, but will be later valuable for assessing the performance of the method. In this case, the ground truth (absolute) transformation $T_Q^{P}$ from $\{P\}$ to the optical tracker reference frame $\{Q\}$ are provided by the optical tracking system, and the transformation $T_{Ref}^{Q}$ from $\{Q\}$ to the reference frame $\{Ref\}$ should also be computed.

Since $T_{Ref}^{S_i}*T_{S_i}^{P}=T_{Ref}^{Q}*T_Q^{P}$ forms an AX=YB problem, the unknown transformations can be easily computed using various well-established hand-eye calibration techniques, such as a concurrent nonlinear optimization used in this work. Consequently, the instrument's pose is measured via each sensor as $T_{Ref}^{P}=T_{Ref}^{S_i}*T_{S_i}^{P}$ and observed via the ground truth as $T_{Ref}^{P}=T_{Ref}^{Q}* T_Q^{P}$ for assessment.

To simplify the notations, from this point onward the reference frames are omitted as all vectors are only expressed in the frame $\{Ref\}$.

2) Temporal Parameters

Quantification of temporal parameters is also necessary if multiple tracking devices are used, and they do not share accurate external hardware synchronization. In this case, the redundant measurements are not reported concurrently, and temporal parameters should be computed to determine the relative latency between time-stamps of various sensors. These parameters can then be used to ensure redundant observations match at any given time-stamp. In this work, a single EM tracking device connects to all EM sensors and provides synchronized measurements. Therefore, there is no need to quantify the temporal parameter. However, in order to validate the proposed approach with the ground truth optical tracker, a constant latency is estimated using correlation analysis and applied to synchronize the EM measurements with the measurements of the optical tracker.

3) Error Parameters

It is also important to quantify the EM measurement error in order to provide the uncertainty associated with each sensory observation in real-time. In general, EM measurements contain nonuniform error distributions over the tracking volume; therefore, systematic (bias) and random (jitter) errors need to be characterized in terms of both position and orientation of the sensor. However, in this work, the minor impact of orientation is neglected, and measurement uncertainties are computed only as a function of sensor position $d_{Si}=[x_{S_i} y_{S_i} Z_{S_i}]^T$.

For convenience, a robotic platform was employed to place the sensors at various positions in the workspace, and the measurement error at each position was determined using ground truth (i.e., optical tracker) observations. During this process, the robotic manipulator was placed away from the EM tracking volume to avoid additional field distortion. As an alternative, error characterization can be performed just as easily with a calibration phantom or manual positioning.

First, systematic errors are modeled and compensated using a robust (bisquare reweighting) second-order polynomial multilinear regression (Holland, P. W., et al., *Communications in Statistics-Theory and Methods*, 6:813-827, 1977) as a function of sensor position. This is primarily performed to remove the measurement bias, if any, resulting in zero-mean error distributions. Next, random errors characterizing measurement uncertainty can be modeled as zero-mean normally distributed random variables. (This assumption is validated, see FIGS. 4A and 4B.) The associated variance $\sigma^2_{S_i}$ is modeled for each degree-of-freedom (DOF) seperately, since the measurement error is not isotropic. The variance $\sigma^2_{S_i}$ is then modeled as:

$$\sigma^2_{S_i} = \Psi(d_{si}, \delta_i, Q_i) \quad (1)$$

where $d_{si}$ is the sensor position, $\delta_i$ is the Frobenius norm of the transformation discrepancy matrix, indicating deviations from the fixed known configurations of the sensors, and $Q_i$ is the signal quality (distortion) measure provided by the tracking device, indicating the extent to which the measurements are reliable. The coefficients (weights) of $\Psi$ were quantified using the same robust regression method (Holland, P. W., et al., 1977). Once these coefficients are found, the variance can be computed in real-time.

B. Simultaneous Tracking and Calibration

Once the parameters of the experimental setup are known, simultaneous tracking and calibration can be achieved. In contrast to the system identification, this step is performed in real-time (e.g., intra-operatively) and carried out in the clinical environment with the presence of field distorting objects. The step is the core of the SLAM process, and the objective is to create and update a field distortion map in order to dynamically calibrate for systematic errors while tracking the instrument. A probabilistic extended Kalman filter (EKF) SLAM algorithm was formulated to simultaneously estimate the pose of the tracked instruments and update the parameters of the field distortion model.

1) Preliminary

For an arbitrary frame attached to the tracked instrument, let $d_p=[x_p y_p z_p]$ denote the position vector, with $\dot{d}_p$ representing the linear velocity. Also, let $q_p=[q_0\ q_1\ q_2\ q_3]$ denote the orientation (quaternion), with $\omega_p=[\omega_x\ \omega_y\ \omega_z]$ representing the angular velocity. Given the sampling time $T_s$ at each discrete time step $k=1, 2, \ldots, K$, the state vector describing the pose and velocity of the tool is defined as $x_k=[d_{p(k)}\ q_{p(k)} \dot{d}_{p(k)} \omega_{p(k)}]^T$. It is assumed that an initial state value $x_0$ is given, and the remaining values $x_{1:K}$ are to be recovered.

In order to compensate for field distortion, the measurement error should be represented based on the position of the EM sensor in the workspace. For each DOF j, the field distortion can be modeled with a distortion estimator function $\Omega_j(d_{Si})$ describing measurement error (bias) as a function of sensor position $d_{Si}$. This distortion function is based on a multivariate Gaussian function, allowing for a continuous and differentiable map, with a distortion map vector $m_j$ defined to contain the parameters (coefficients) of $\Omega_j$. Let also m be the set of all field distortion map parameters ($m_j$ parameters for all DOB), and $\Omega(d_{Si})$ be the set of all the $\Omega_j$. Therefore, $\Omega$ can estimate the field distortion in the vicinity of each sensor position, once given the state x and the parameters m. The estimated bias values can then be compensated for each sensor.

2) SLAM Formulation

Given sensory observations z including the measurements of all the EM sensors along with the spatial parameters (transformations $T_{S_i}^P$), the EKF-SLAM algorithm can be used to estimate the state x and the parameters m. For that, the EKE-SLAM requires the formulation of a motion model as well as an observation model.

The motion model is used for prediction $P(x_k|x_{k-1})$ and describes the state transitions as expressed in (2). The state transition is assumed to be a Markov process, such that $x_k$ depends only on the previous state $x_{k-1}$ and not the entire history $X_{0:k-1}$.

The observation model is then used to correct this prediction, by describing the probability of making sensory observations $z_k$ given the state and the map parameters $P(z_k|x_k, m_k)$. Therefore, the observation model establishes a relationship between the observations $z_k$ and the map parameters for the current state as expressed in (3).

$$x_k = f(x_{k-1}) + w_k \quad (2)$$

$$z_k = h(x_k, m_k) + v_k \quad (3)$$

In these models, $w_k \sim \mathcal{N}(0, Q)$ is a Gaussian random vector with a constant covariance Q describing uncertainty in the state transitions, while $v_k \sim \mathcal{N}(0, R_k)$ is a Gaussian random vector with an estimated covariance $R_k(\sigma^2_{S_i}{}^{(k)})$ describing uncertainty in measurements computed in real-time for each time step k.

Given the state vector $x_k$ and the map parameters $m_k$, the functions $f(\cdot)$ and $h(\cdot)$ along with their covariance matrices Q and $R_k$ are formulated based on a white noise acceleration model with quaternion representation as expressed in (4). In this formulation, the skew symmetric matrix $\phi$ is given by (5).

$$\begin{bmatrix} d_{p(k)} \\ q_{p(k)} \\ \dot{d}_{p(k)} \\ \omega_{p(k)} \end{bmatrix} = \begin{bmatrix} d_{p(k-1)} + T_s \dot{d}_{p(k-1)} \\ e^{T_s \phi(\omega_{p(k)})} q_{p(k-1)} \\ \dot{d}_{p(k-1)} \\ \omega_{p(k-1)} \end{bmatrix} \quad (4)$$

-continued $$\phi(\omega) = \frac{1}{2}\begin{bmatrix} \omega \times & \omega \\ -\omega^T & 0 \end{bmatrix} \quad (5)$$

3) EKF-SLAM Solution

Properties of EKF-SLAM are described in Thrun, S., et al., *Probabilistic Robotics*, MIT press, 2005. Particularly, this formulation assumes that probability distributions can be represented by their first ($\mu_k$) and second ($\Sigma_k$) moments (13).

$$P(x_k, m_k | z_{1:k}, x_0) \sim \mathcal{N}(\mu_k, \Sigma_k) \quad (6)$$

Therefore, given an initial value $x_0$ and the set of all the observations $z_{1:k}$, an EKF-SLAM is then applied to compute the mean $\mu_k = [\hat{x}_k \, \hat{m}_k]^T$ (with ˆ representing the best estimate at time step k) and the covariance $\Sigma_k$ (representing uncertainties associated with the best estimate) of the joint posterior distribution $P(x_k, m_k | z_{1:k}, x_0)$ as given in (7) and (8).

$$\mu_k = \begin{bmatrix} \hat{x}_k \\ \hat{m}_k \end{bmatrix} = E\left[\begin{pmatrix} x_k \\ m_k \end{pmatrix} \bigg| z_{1:k}\right] \quad (7)$$

$$\Sigma_k = \begin{bmatrix} \Sigma_{xx} & \Sigma_{xm} \\ \Sigma_{xm} & \Sigma_{mm} \end{bmatrix} = E\left[\begin{pmatrix} x_k - \hat{x}_k \\ m_k - \hat{m}_k \end{pmatrix}\begin{pmatrix} x_k - \hat{x}_k \\ m_k - \hat{m}_k \end{pmatrix}^T \bigg| z_{1:k}\right] \quad (8)$$

Considering $X_k = [x_k \, m_k]^T$ as the full joint state vector, and $F(X_k) = [f(x_k) m_k]^T$ as the joint state motion model, the time update (prediction) equations are given in (9) and (10). In these equations, $\nabla F$ is the Jacobian of F with respect to X evaluated at $\mu_{k-1}$ as expressed in (11), $$\bar{\mu}_k = F(\mu_{k-1}) \quad (9)$$

$$\bar{\Sigma}_k = \nabla F \Sigma_{k-1} \nabla F^T + Q \quad (10)$$

$$\nabla F_{[i,j]} = \frac{\partial F_{[i]}}{\partial X_{[j]}}\bigg|_{\mu_{k-1}} \quad (11)$$

Given the measurements, the observation update (correction) equations are expressed in (12) and (13). In these equations, $\nabla h$ is the Jacobian of h with respect to X evaluated at $\bar{\mu}_k$ as given in (16), and $\mathcal{K}$ is the Kalman filter gain (14).

$$\mu_k = \bar{\mu}_k + \mathcal{K}_k(z_k - h(\bar{\mu}_k)) \quad (12)$$

$$\Sigma_k = \bar{\Sigma}_k - \mathcal{K}_k S_k K_k^T \quad (13)$$

$$\mathcal{K}_k = \bar{\Sigma}_k \nabla h^T S^{-1} \quad (14)$$

$$S_k = \nabla h \bar{\Sigma}_k \nabla h^T + R_k \quad (15)$$

$$\nabla h_{[i,j]} = \frac{\partial h_{[i]}}{\partial X_{[j]}}\bigg|_{\bar{\mu}_k} \quad (16)$$

C. Experimental Validation

The performance of the field distortion compensation method was experimentally assessed for unconstrained 6 DOF motion tracking, detailed in this section.

1) Experimental Setup

An Ascension (Burlington, Vt., USA) 3D guidance trakSTAR was used for the EM tracking measurements. In contrast to alternating current (AC) varying field generators, the Ascension transmitter generates direct current (pulsed-DC) EM fields in order to suppress the interference caused by the induced eddy currents in nearby conductive field distorting metals. However, as it will be shown in the results, this system is still unable to compensate for the distortion caused by ferromagnetic objects, such as the ones used in this experiment.

Figure 2A:
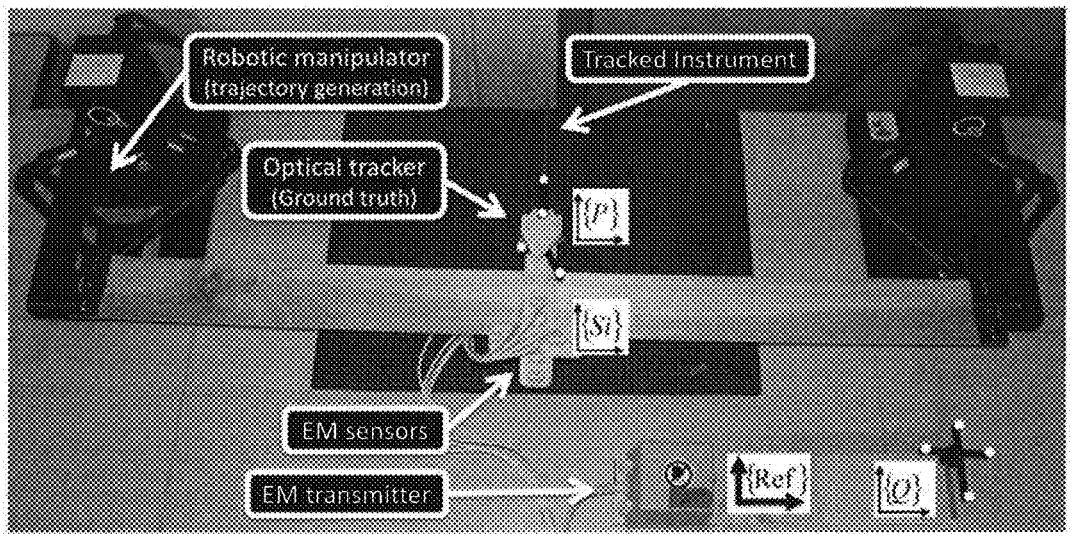
FIG. 2A is a photograph of an experimental setup, showing relevant coordinate systems, including tracked frame $\{P\}$ on the target, EM sensor frame $\{S_i\}$, EM reference frame $\{Ref\}$, and optical reference frame $\{Q\}$.
Figure 2B:
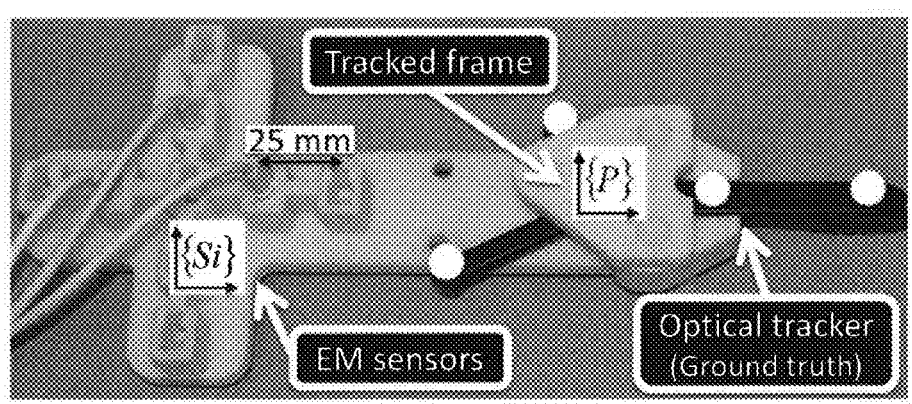
FIG. 2B is a photograph showing a tool used to hold EM sensors and an optical marker, used in experimental setups for assessment and validation.
Figure 2C:
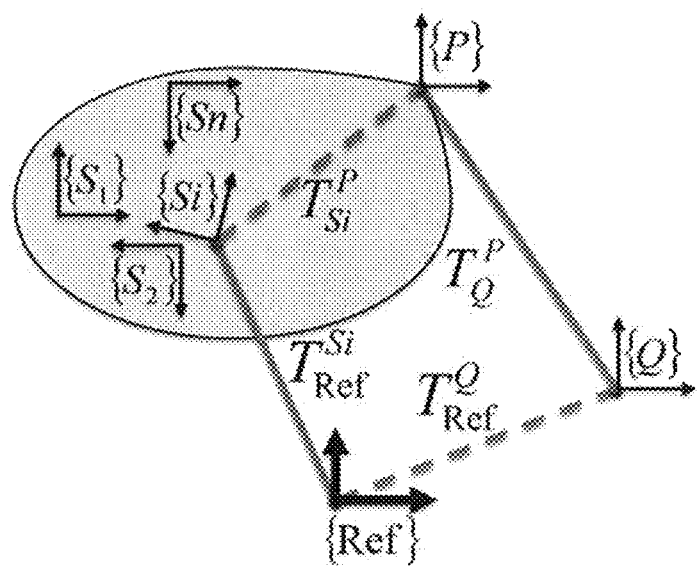
FIG. 2C is a diagram showing coordinate systems and transformations, with redundant EM sensors ($S_1, S_2 \ldots S \ldots, S_n$) used to track the target frame $\{P\}$, and spatial transformations.

The experiment relies on two redundant measurements; thus, three Model 800 (8×8×20 mm) EM sensors $\{S_i\}$, (i=1, 2, 3) provide 6 DOF measurements to the SLAM algorithm for dynamic target $\{P\}$ tracking and field distortion compensation. As shown in FIGS. 2A and 2B, these EM sensors were mounted on a rigid tool designed to firmly hold the sensors. The tool also provided various sensor mounting options. FIG. 2B shows the configuration used in this experiment. The tool also held an optical tracker to allow ground truth observations for the tracked frame $\{P\}$. Note that optical tracker is not part of the SLAM process; it is used only for validation and provides ground truth measurements. The measurements were collected using an NDI (Waterloo, ON, Canada) Polaris Spectra.

To facilitate spatial and temporal calibration, the tool can also be driven using two parallel robotic manipulators, providing arbitrary and repeatable motion trajectories. These manipulators (shown in FIG. 2A) are not part of the SLAM process; they are used only during system identification step to quantify sensor parameters (pre-operatively), and will be used in future to explore the impact of various speeds and motion profiles on the performance of the method. The robotic manipulators were placed outside the tracking volume and ~70 cm away from the transmitter, to avoid introducing additional field distortion.

The complete experimental setup is shown in FIG. 2A. It should be noted that this setup is not meant to resemble any clinical procedure; it only serves as a platform to validate and study the performance of the method.

2) Experimental Procedure

The system identification step was performed off-line (pre-operatively) in a controlled environment free from field distorting objects, in order to quantify spatial, temporal, and error parameters of the sensors. Using the robotic platform, the tool was first oscillated with an up-chirp trajectory in the frequency range of 0.1 to 25 Hz for a period of 12 seconds, in order to estimate and compensate for the acquisition latency (temporal parameter) between measurements of the EM sensors and those of the ground truth optical tracker. The kinematic parameters were subsequently quantified using 63 poses spanning the workspace. Once the temporal and spatial parameters were computed, the robotic platform was employed to place the EM sensors at a total of 189 positions (a rectilinear grid 9×7×3 with 25 mm spacing) in the workspace, in order to determine the measurement error at each position. Using (1) and the ground truth (i.e., optical tracker) observations, the measurement uncertainties ($\sigma^2_{S_i}$) were modeled, and the systematic errors were modeled and compensated.

Experiments were next performed to assess the effectiveness of the SLAM method for field distortion compensation during free 6 DOF motions. To introduce EM field distortion, a block of steel (10×30×50 mm) was centered at ~$[250 \; 200 \; 0]^T$ mm in the transmitter's reference frame $\{Ref\}$. It should be noted that steel highly distorts the EM field, as it is both ferromagnetic ($\mu r \approx 4000$) and conductive ($\sigma \approx 4$ MS/m). The data from the EM sensors and the ground truth optical tracker were recorded at a rate of 60 Hz (sampling time) while the instrument was in freehand motion, and the proposed method for simultaneous tracking and field distortion compensation was applied.

A. System Identification

The 12-second chirp trajectory produced 720 data samples (per sensor) with the tool speed ranging from 34 to 307 mm/s. For the temporal parameter, a constant latency of 49±6 ms was computed using eight different data sets. It is noted that inaccurate temporal parameter quantification results in undesired positional error at high speed motions, For example, a 10 ms temporal calibration error results in 1 mm position error if the instrument moves at the speed of 100 minis. Consequently, ground truth measurements cannot be provided accurately by the optical tracker at high speed motions. Therefore, in this experiment, high speed motions were precluded to avoid complexities arisen from such inaccuracies and other undesired dynamic measurement behavior.

Once the temporal lag was compensated, spatial parameters were computed, resulting in 4 homogenous transformation matrices (17-20).

$$T_{S_1}^P = \begin{bmatrix} -0.99 & +0.03 & +0.03 & -10.80 \\ -0.02 & +0.00 & -0.99 & +195.62 \\ -0.03 & -0.99 & -0.00 & +1.64 \\ 0 & 0 & 0 & 1 \end{bmatrix} \quad (17)$$

$$T_{S_2}^P = \begin{bmatrix} -0.99 & +0.02 & +0.03 & -10.46 \\ -0.03 & +0.00 & -0.99 & +220.97 \\ -0.02 & -0.99 & -0.00 & -24.79 \\ 0 & 0 & 0 & 1 \end{bmatrix} \quad (18)$$

$$T_{S_3}^P = \begin{bmatrix} -0.99 & +0.03 & +0.03 & -11.19 \\ -0.02 & +0.00 & -0.99 & +220.75 \\ -0.03 & -0.99 & -0.00 & +25.81 \\ 0 & 0 & 0 & 1 \end{bmatrix} \quad (19)$$

$$T_{Ref}^Q = \begin{bmatrix} +0.02 & -0.03 & -0.99 & -112.78 \\ +0.00 & -0.99 & +0.02 & -246.87 \\ -0.99 & +0.00 & -0.01 & -18.72 \\ 0 & 0 & 0 & 1 \end{bmatrix} \quad (20)$$

Figure 3:
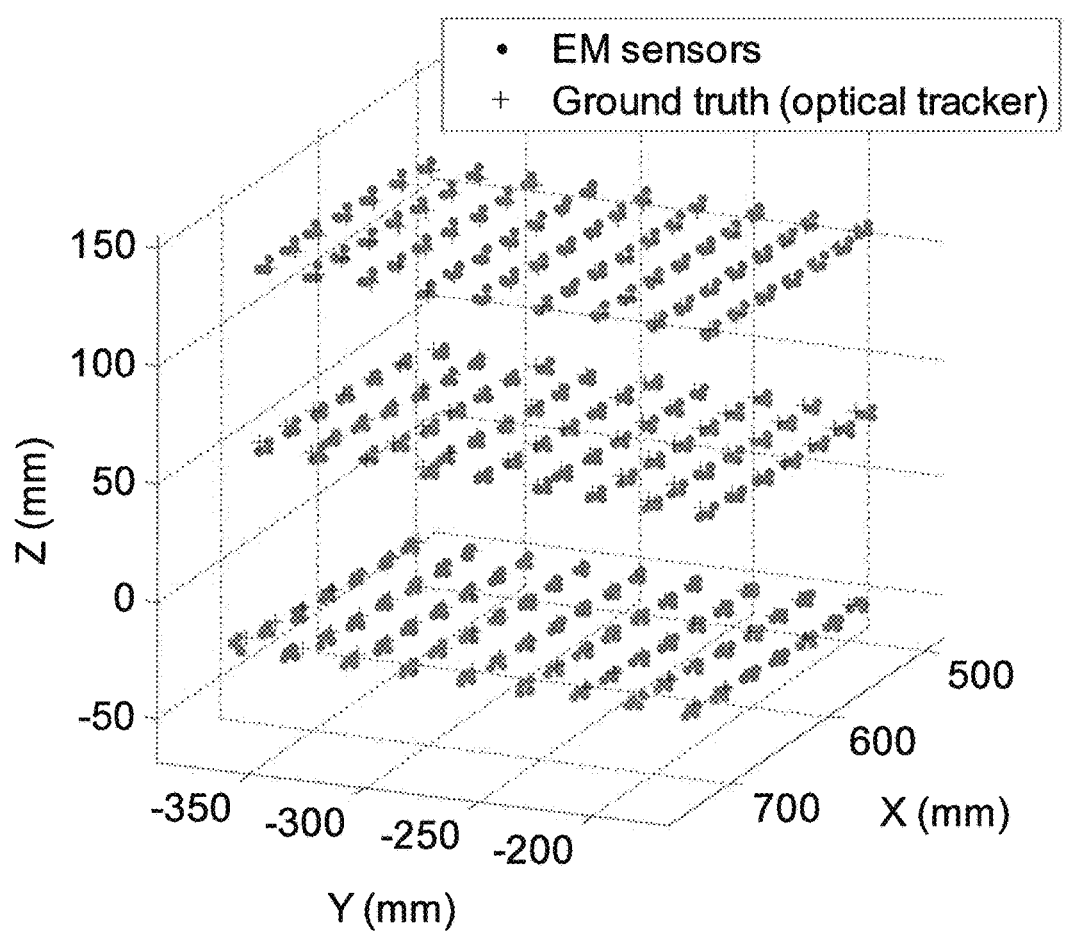
FIG. 3 is a plot showing ground truth optical tracker observations provided for a tracked target frame $\{P\}$ via spatial transformations (hand-eye calibration), used to model EM measurement uncertainties as described in Example 1.

Given the above spatial transformation (20), the optical tracker measurements $T_Q^P$ can be used to provide the ground truth observations $T_{Ref}^P = T_{Ref}^Q * T_Q^P$ of the tracked frame {P} for assessment. FIG. 3 illustrates these observations for the 189 grid points used to quantify the EM measurement error.

Figure 4A:
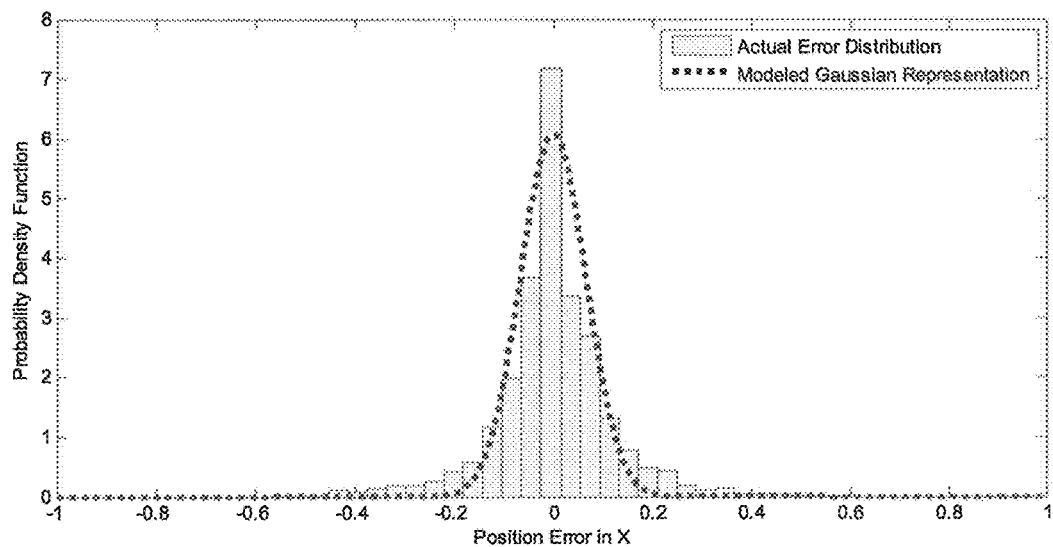
FIGS. 4A and 4B are plots showing samples of measurement error distributions with their corresponding modeled Gaussian representations for measurements of (4A) a translation in X (mm), and (4B) an orientation in A (degree), where A stands for Azimuth in an ZYX Euler angler representation of the rotation matrix, as described in Example 1.
Figure 4B:
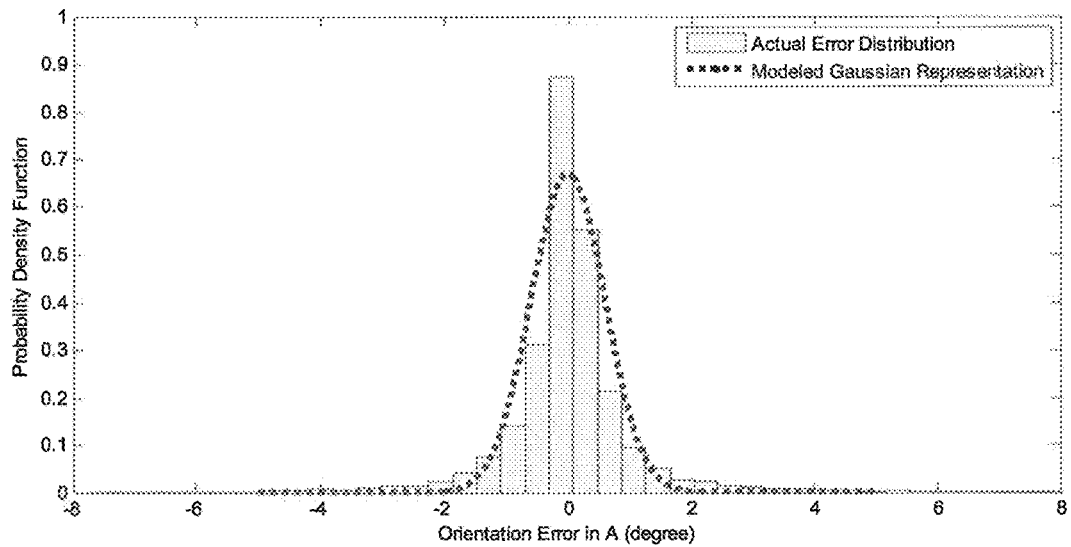

Using the ground truth optical tracker observations, the measurement uncertainties were modeled, and the systematic errors were modeled and compensated resulting in final errors less than 0.4 mm and 5 degrees for translation and orientation measurements, respectively. A sample of the actual error distribution (probability density function) and the modeled Gaussian representation within the workspace is illustrated in FIGS. 4A and 4B.

B. Simultaneous Tracking and Calibration

Figure 5A:
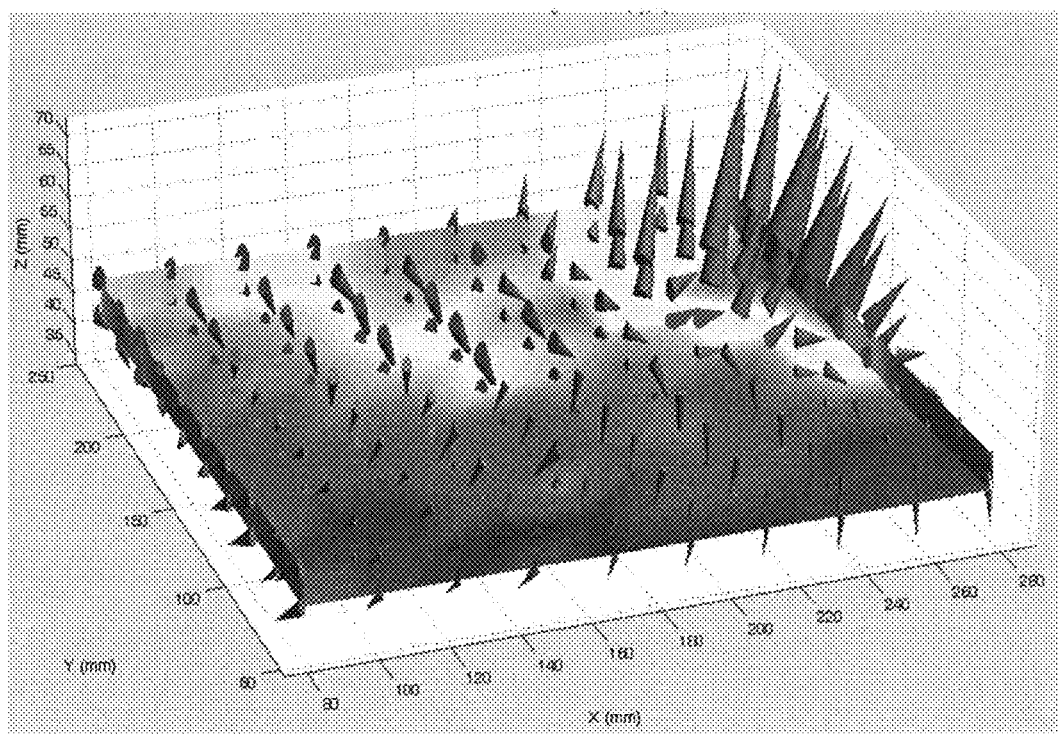
FIGS. 5A and 5B are plots showing field distortion error for 6-DOF, where position field distortion (5A) is represented by [x y z], and orientation field distortion (5B) is represented by [A E R] Euler angles (ZYX), as described in Example 1.
Figure 5B:
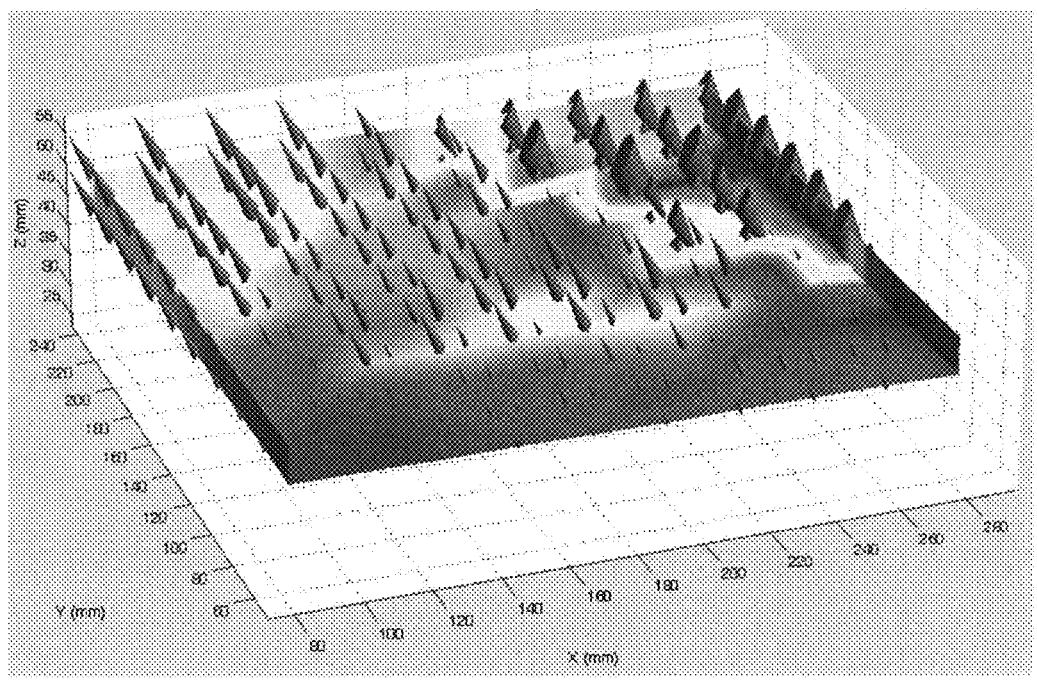
Figure 6A:
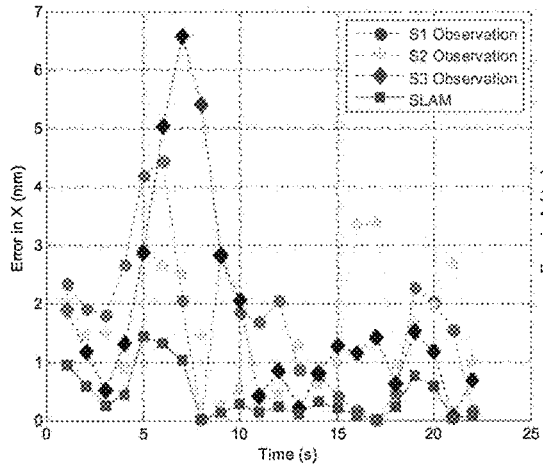
FIGS. 6A-6F are plots of tracking error of SLAM compared to EM sensors, where the left column (6A, 6C, 6E) shows the tracking error in position X, Y, and Z, and the right column (6B, 6D, 6F) shows the tracking error in orientation A, E, R (ZYX Euler angles: Azimuth. Elevation, and Roll) (data was downsampled for clarity), as described in Example 1.
Figure 6B:
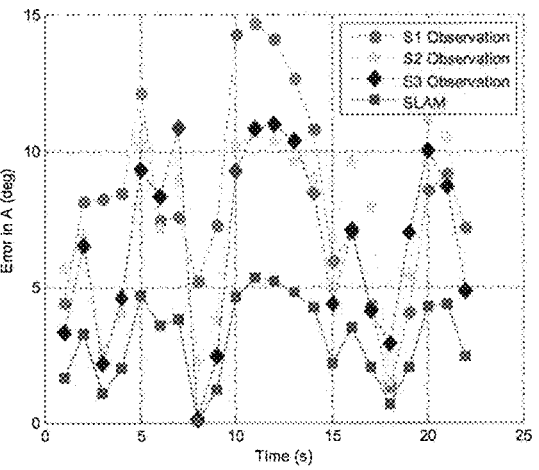
Figure 6C:
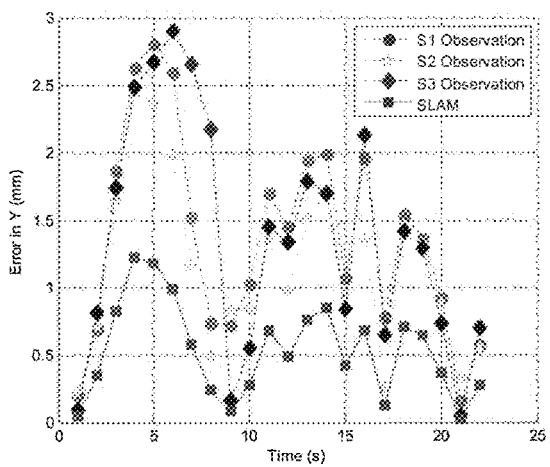
Figure 6D:
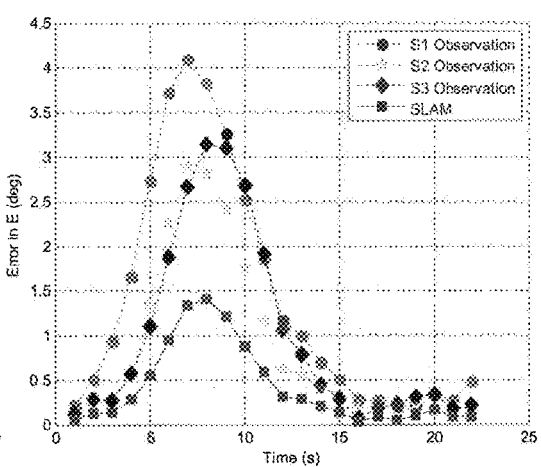
Figure 6E:
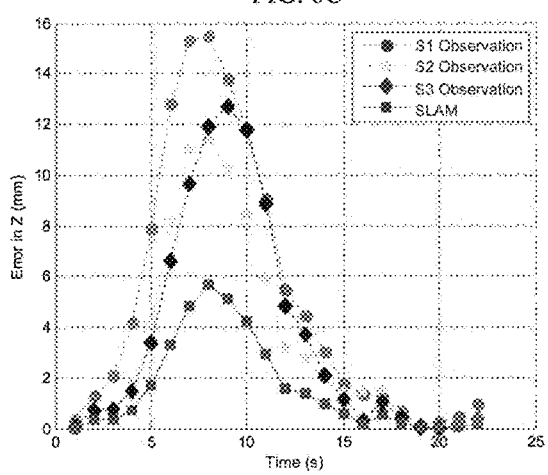
Figure 6F:
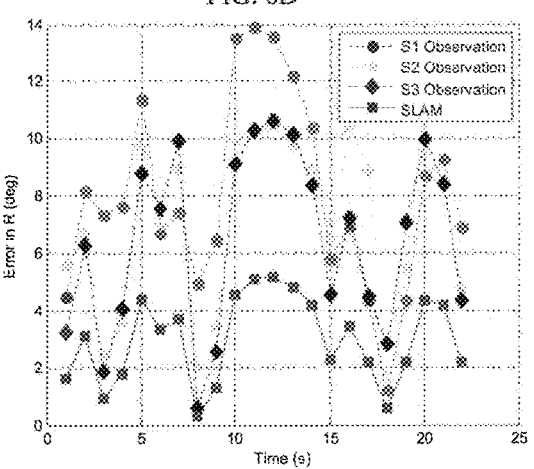

The method for simultaneous tracking and field distortion compensation was applied during the 6 DOF motion of the tool in the presence of the field distorting object (the block of steel). The resulting field distortions are plotted in FIG. 5A for position and in FIG. 5B for orientation. The tracking errors of the EM sensors with and without field distortion compensation are compared in FIGS. 6A-6F. The left column (FIGS. 6A, 6C, and 6E) shows the tracking error in position X, Y, and Z, while the right column (FIGS. 6B, 6D, and 6F) shows the tracking error in orientation A, E, R (ZYX Euler angles: Azimuth, Elevation, and Roll).

Within the workspace, measurement errors were a maximum ~16 mm and ~15 degrees in the presence of the ferromagnetic steel block; while with the SLAM formulation these errors were reduced to maximum of ~6 mm and ~6 degrees. The SLAM tracking error for each DOF is tabulated in Table 1. Using this data, an error reduction of 65±10% for position, and 59±4% for orientation measurements was achieved.

TABLE 1

The SLAM tracking error for each measurement DOF

| Degree of Freedom[a] | Mean | Variance | Minimum | Maximum |
|---|---|---|---|---|
| X | 0.42 | 0.15 | 0.04 | 1.60 |
| Y | 0.57 | 0.11 | 0.01 | 1.31 |
| Z | 1.52 | 3.04 | 0.01 | 5.68 |
| A | 3.24 | 2.67 | 0.12 | 6.46 |
| E | 0.41 | 0.19 | 0.02 | 1.47 |
| R | 3.17 | 2.51 | 0.28 | 6.25 |

[a]Values represent position error in mm or orientation error in degree.

As shown in FIGS. 6A-6F, the SLAM approach provides improved tracking performance in the presence of field distorting objects. Not only does it compensate for systematic field distortion error, but it also minimizes the jitter error, due to its underlying Kalman filter formulation.

For field distortion compensation, there are several major factors that should be considered for practical implementation. These factors include computational complexity, convergence, and performance in dynamic environments.

The classic EKF-SLAM assumes Gaussian distributions and is computationally intensive for large number of map parameters, particularly if more complex field distortion estimators (with more parameters) are used. In fact, the dimension of the covariance matrix is approximately quadratic in terms of the number of the map parameters, and this matrix is updated during the time update (17) and observation update (20) in every time step. The off-diagonal elements of the matrix carry important information and it is shown that the solution may diverge if these elements are ignored. Therefore, to improve the scalability of the EKF-SLAM, extensions such as map decomposition (sub-maps) and alternative representations may be employed. For higher-dimensional systems, or when the Gaussian representation is not valid, more efficient implementations, such as particle filter SLAM (FastSLAM (Montemerlo, M., et al., "Simultaneous localization and mapping with unknown data association using FastSLAM," in *IEEE International Conference on Robotics and Automation (ICRA)*, 2003)), or sparse extended information filters (EIF-SLAM (Thrun, S., et al., *The International Journal of Robotics Research*, 23: 693-716, 2004)) may be preferred.

The convergence is theoretically guaranteed only for linear functions; however, EKF-SLAM uses the Jacobian matrices $\nabla F$ and $\nabla h$ to linearize the motion and observation models. Therefore, the choice of these functions could lead to inaccurate estimations, particularly at some (singular) operating points where the linearized functions do not closely represent the nonlinear function. In this example there was no issue with the linearization and the covariance matrix values consistently converged to lower bounds.

The time varying nature of the SLAM algorithm should also be stressed. Current static pre-calibration techniques may perform satisfactorily if the environment remains stationary. However, in a clinical setting, the movement and operation of devices degrades the quality of the pre-calibration map and distortion compensation becomes less effective. Therefore, the static pre-calibration performance degrades over time, and re-calibration is necessary at least over the region of interest. In contrast, in the SLAM approach described herein, the calibration improves over time. As more observations are made by the EM sensors, the distortion map and the pose of the instrument estimations become more reliable. For highly dynamic environments, further optimization in the SLAM algorithm may be carried out.

EXAMPLE 2

Electromagnetic Tracking for Catheter Path Reconstruction

Accurate catheter tracking is required for various procedures such as high dose rate (HDR) prostate brachytherapy, where catheter path reconstruction is a necessary step to optimize the position of the radioactive source and the dwell times. Electromagnetic (EM) tracking has been introduced in order to overcome the limitations of path reconstruction using standard imaging modalities. However, EM measurements are noisy and subject to distortion in clinical settings. While several error minimization techniques have been proposed, the tracking error still poses a challenge in accurate path reconstruction. Presented herein is a novel filtering technique that incorporates the nonholonomic motion constraints of the EM sensor in the catheter path.

The motion of the sensor in the catheter is nonholonomic, as the sensor is assumed to move along the catheter path. A Kalman filter (KF) was used to integrate the nonholonomic motion of the EM sensor with the raw measurement data. Performance of this approach was validated using an Ascension trakSTAR (Ascension Tech. Corp., Milton, Vt.) and a 6 degrees of freedom (model 55) sensor. A 3D printed calibration phantom firmly held 30 cm long catheters into predefined pound truth paths. The experimental setup was placed in an environment with field distorting objects resembling clinical interferences. The EM sensor measurements were recorded while it was inserted and retracted into the path. Raw measurement data were applied to the method to improve the tracking performance. Results were compared with filtered data provided by the manufacturer.

For the raw measurement data, the root-mean-square (RMS) error along the path was 5.6 mm, and was 2.4 mm with filters provided by the manufacturer. Using the KF with the nonholonomic motion model, the RMS was reduced to 1.8 mm, as tabulated in Table 2.

TABLE 2

Path reconstruction accuracy

| | Raw measurements | Standard manufacturer filter | Nonholonomic Kalman filter |
| --- | --- | --- | --- |
| Minimum error | 0.0 mm | 0.1 mm | 0.0 mm |
| Maximum error | 23.4 mm | 7.0 mm | 5.8 mm |
| RMS error | 5.6 mm | 2.4 mm | 1.8 mm |

Compared to other filtering methods, this approach has the advantage of exploiting the additional orientation measurements in its formulation. This information combined with the position measurements successfully improves the accuracy of path reconstruction. Thus, filtering using a nonholonomic model is expected to improve clinical procedures requiring the reconstruction of catheter path such as HDR brachytherapy.

EXAMPLE 3

Nonholonomic catheter path reconstruction using electromagnetic tracking

Catheter path reconstruction is required in various minimally-invasive procedures, such as cardiovascular interventions and high-dose-rate (HDR) brachytherapy. The success of such procedures depends heavily on accurate determination of the catheter paths. While catheters are usually inserted under ultrasound guidance, a post-implantation scan, usually with CT technology, is performed to accurately localize the catheter relative to the target area. Catheter path reconstruction using these standard imaging modalities has a number of limitations, including radiation exposure and catheter displacements during patient transfer from the scanner to the operating room. Complementary electromagnetic (EM) tracking has been introduced in order to overcome these limitations.

EM tracking technology allows sensor measurements inside the human body without line-of-sight restrictions. Miniaturized sensors are directly inserted into the catheter to reconstruct the path. However, EM measurements are noisy and subject to interference present in clinical environments. Indeed, several studies have shown that measurement uncertainty may vary considerably depending on the clinical setup. To reduce tracking errors due to environmental interference, some manufacturers deployed direct current (DC) tracking systems. These systems measure the pose of the sensor relative to the transmitter once the magnetic field is stabilized. As a result, and compared to alternative current (AC) based systems, DC-based tracking systems do not suffer from eddy current interferences induced in conductive objects. However, these systems are still susceptible to magnetic field distortions caused by objects (such as those with ferromagnetic properties) surrounding the tracking volume. Hence, accurate path reconstruction using EM tracking remains challenging. Various techniques have been proposed to minimize measurement error, such as sensor fusion, static calibration of the tracking system, and filtering using motion models such as needle deflection estimations. While these techniques may allow some reduction of the tracking error, they have generalized formulations. Therefore, tracking error can be further minimized by means of a specific filter designed for catheter path reconstruction.

In this example, a filtering approach is described that was designed specifically for catheter path reconstruction. Path reconstruction with respect to a reference sensor {Ref} was achieved by threading a miniature EM sensor {Cath} within the catheter. To reduce EM tracking error, an extended Kalman filter (EKF) was used to integrate both the position and orientation EM measurements with the nonholonomic motion constraints of the sensor along the catheter. The experimental setup in a UDR suite included the stepper and TRUS probe, with the EM tracking system's reference coordinate frame {EMS} attached to the field transmitter, and {Ref} attached to the reference sensor.

In contrast to conventional filtering techniques that rely only on position measurements, this embodiment uses both position and orientation measurements as well as the nonholonomic motion constraint, in order to accurately reconstruct the catheter paths.

Filter Formulation
Extended Kalman Filter

An EKF was employed to estimate the state vector defined at a discrete time step k as:

$$X_k = [x_k\ y_k\ z_k\ a_k\ e_k\ r_k]^T \quad (21)$$

where $^T$ denotes transpose, containing the position coordinates x, y, z and orientations a, e, r (expressing the azimuth, elevation, and roll Euler angles respectively) of the sensor in the default tracker's coordinate system {EMS}. In essence, the EKF formulation uses a process model for prediction and a measurement model for correction to minimize the estimation error covariance.

The process model is governed by the non-linear stochastic difference equation, describing the state transition as:

$$X_k = f(X_{k-1}) + \varphi_k \quad (22)$$

where f defines the motion kinematic with the nonholonomic constraint introduced in the next section, and $\varphi_k$ is considered as the process noise, defining the uncertainties of the process model. The process noise is assumed to be constant during each sampling interval, and $\varphi_k$ is considered to have a zero mean Gaussian distribution with a covariance Q, computed as:

$$Q = \sigma_q^2 * I \quad (23)$$

where $\sigma_q^2$ is the variance and indicates the process uncertainty estimation (Sadjadi, H., et al., "Fusion of electromagnetic trackers to improve needle deflection estimation: simulation study," IEEE Transactions on Biomedical Engineering, 60:2706-2715, 2013). In order to correct for the estimation made by the process model, the measurement equation relates the state vector to the measurement $z_k$, and it can he formed as:

$$z_k = HX_k + v_k \quad (24)$$

with H=I, the identity matrix. The measurement noise, denoted by $v_k$, and the measurement noise covariance matrix R were updated at each iteration step according to:

$$R = \sigma_r^2 * I \quad (25).$$

The variance $\sigma_r^2$ is computed and updated based on the sensor signal quality at each time step to represent the precision of the measurements.

Nonholonomic Process Model

In catheter path reconstruction, the sensor's kinematics have nonholonomic constraints equivalent to that of a generalized unicycle in 3-dimensional space. The nonholonomic constraint restricts lateral motion along the path. Therefore, the position of the sensor inside the catheter can be estimated using these nonholonomic motion constraints in conjunction with both the position and orientation EM measurements. Accordingly, the kinematics of the sensor can be inferred from its linear and angular velocities.

The position and orientation (pose) of the sensor in the tracker's coordinate system {EMS} can be represented with the following 4×4 homogeneous transformation matrix:

$$X_k = \begin{bmatrix} R_k & P_k \\ 0 & 1 \end{bmatrix} \quad (26)$$

where $R_k$ is the associated 3×3 rotation matrix describing the orientation of the sensor based on the Euler angles a, e, r, and $P_k = [x\ y\ z]^T$ is the 3×1 vector representing its position.

Figure 7:
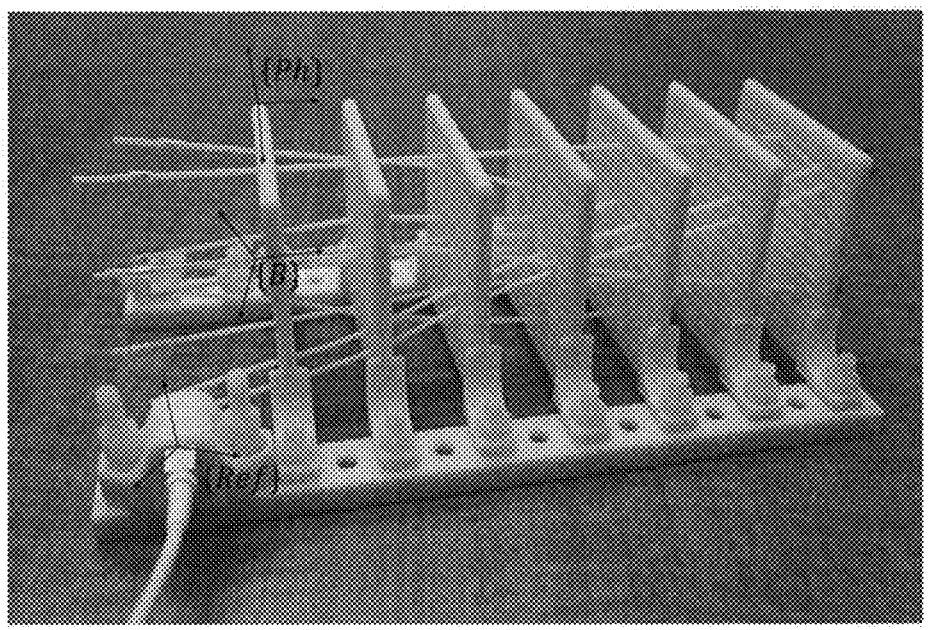
FIG. 7 is a photograph showing a phantom holding ten catheters in predefined ground truth paths, with the body coordinate system $\{B\}$ located at a sensor tip, a global coordinate frame $\{Ref\}$ located on a reference sensor, and a local coordinate frame on the phantom $\{Ph\}$.

FIG. 7 is a photograph showing a phantom holding ten catheters in predefined ground truth paths. The fixture was designed in CAD and 3D printed with an accuracy of about 0.25 mm. An EM sensor is inserted into the catheter. The body coordinate system {B} is located at the sensor tip. The global coordinate frame {Ref} is located on the reference sensor. The local coordinate frame on the phantom {Ph} is also represented.

Figure 8:
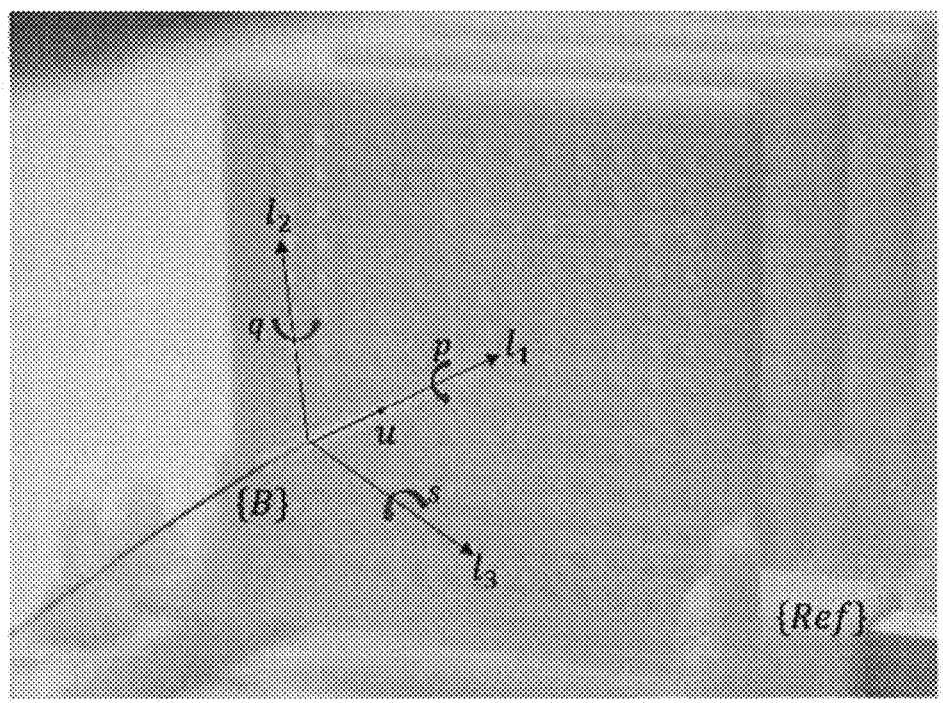
FIG. 8 is a photograph showing a body-fixed coordinate system $\{B\}$ located at a tip of a sensor inserted inside a catheter, with the longitudinal linear velocity u, and the rotation rates p, q, s indicated.

FIG. 8 is a photograph showing the body-fixed coordinate system {B} located at the sensor tip. The longitudinal linear velocity u, and the rotation rates p, q, s are characterized.

In the body coordinates system {B} (FIGS. 7 and 8), the twist $\vartheta_k$ of the sensor can be represented by the following notation:

$$\vartheta_k = [u\ v\ w\ p\ q\ s]^T \quad (27)$$

where u, v, w are the sensor's linear velocities in {B}, and p, q, s express the body-fixed rotation rates, as shown on FIG. 8.

Due to the nonholonomic constraints, only the longitudinal linear velocity and the angular velocities are taken into account. Therefore, the lateral velocities are equal to zero (v=w=0), and the twist $\vartheta_k$ can take the following homogeneous transformation matrix notation:

$$V_k = \begin{bmatrix} 0 & -s & q & u \\ s & 0 & -p & 0 \\ -q & p & 0 & 0 \\ 0 & 0 & 0 & 0 \end{bmatrix}. \quad (28)$$

The transformation between the body's coordinate and the tracker's coordinate systems can then be described by relating the velocity $\dot{X}$ of the sensor in {EMS} with the twist V of the sensor in {B}:

$$\dot{X} = X * V \quad (29)$$

where the solution to this differential equation is given by:

$$X_{k+1} = X_k * \exp(dt * V_k) \quad (30)$$

with dt the sampling time between the steps k and k+1.

Experimental Validation

To evaluate the performance of this approach, the experimental setup replicated a prostate HDR brachytherapy scenario as one of the possible options. The phantom consisted of a series of parallel rectangular grids to allow a large number of known catheter configurations (FIGS. 7 and 8).

Ten catheters 15ga "flexineedle" (Best Medical International Inc., Springfield, Va.) were held in position by the 3D-printed phantom with predefined paths (FIG. 7). Given its known configuration, each catheter path was represented as a set of points, whose homogeneous coordinates $_{ph}P$ were expressed in the phantom's local coordinate frame {Ph} (FIG. 7). Therefore, {Ph} was registered in order to express these ground truth positions in the reference coordinate frame. To do so, the optimized translation $\hat{T}$ and rotation $\hat{R}$ matrices that align {Ph} to {Ref} were computed using Arun's method (Arun, K. S., et al., "Least-squares fitting of two 3-D point sets," Pattern Analysis and Machine Intelligence, IEEE Transactions 5:698-700, 1987). Therefore, the corresponding ground truth positions $_{Ref}P_{GT}$ were computed by:

$$_{Ref}P_{GT} = \hat{R} *_{Ph}P + \hat{T} \quad (31)$$

For convenience in the notations, variables are expressed in the reference coordinate system. Hence, the ground truth positions $_{Ref}P_{GT}$ are referred to as $P_{GT}$.

Using the DC-based "3D Guidance trakStar" electromagnetic tracking system (Ascension Tech. Corp., Milton, Vt.), a 6 degrees-of-freedom (Model 55) sensor was inserted into the catheter paths (FIG. 8). Experimental data were collected in a research environment, involving minor field distortion interferences from surrounding objects.

Performance Evaluation

For performance metrics we considered a reconstruction error $err_j$ for each estimated position $\hat{P}_j$ with $j=1, 2, \ldots, N$ and N is the number of measurement samples recorded during the insertion of the EM sensor within each catheter path. The reconstruction error $err_j$ was defined as the Euclidean distance between each $\hat{P}_j$ and the closest ground truth position $P_j$. Therefore, $$err_j = \|P_j - \hat{P}_j\| \quad (32).$$

Given err, the set of all the $err_j$, the accuracy of each reconstruction was evaluated by computing the root-mean-square (RMS) of err, and the precision of each reconstruction was evaluated by computing the standard deviation ($\sigma$) of err. As a result, $$\sigma = \sqrt{\frac{1}{N-1} \sum_{j=1}^{N} (err_j - \overline{err})^2} \quad (33)$$

with $\overline{err}$ representing the mean of err,

In addition, the 95% confidence interval (CI), minimum and maximum error of each complete path reconstruction were computed. The means of these factors over the ten path reconstruction were also calculated (see Table 3), and two-sample t-tests were conducted to determine the statistical difference between the path reconstruction accuracies.

TABLE 3

Mean results over ten path reconstructions.

| Error | Raw measurements | Standard manufacturer filter | Nonholonomic extended Kalman filter |
|---|---|---|---|
| RMS | 3.7 mm | 3.3 mm | 2.7 mm |
| 95% CI | 6.8 mm | 6.0 mm | 4.5 mm |
| Minimum | 0.5 mm | 0.4 mm | 0.9 mm |
| Maximum | 7.8 mm | 8.8 mm | 5.2 mm |
| Standard deviation | 1.8 mm | 1.6 mm | 1.1 mm |

Reconstruction using the Raw Sensor Measurements

Figure 9A:
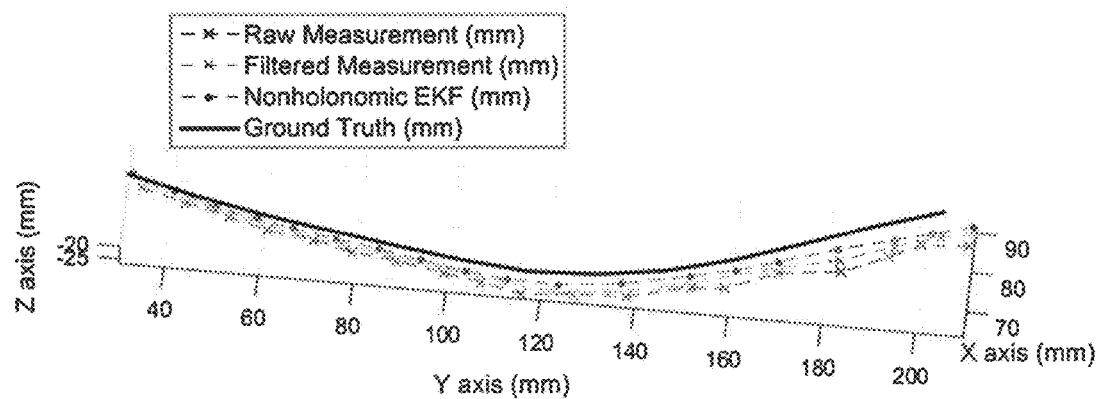
FIG. 9A is a plot showing a sample of catheter path reconstruction with raw measurement data, using the manufacturer's filter, and using a nonholonomic EKE filter according to one embodiment (data points were downsampled for graphic clarity).
Figure 9B:
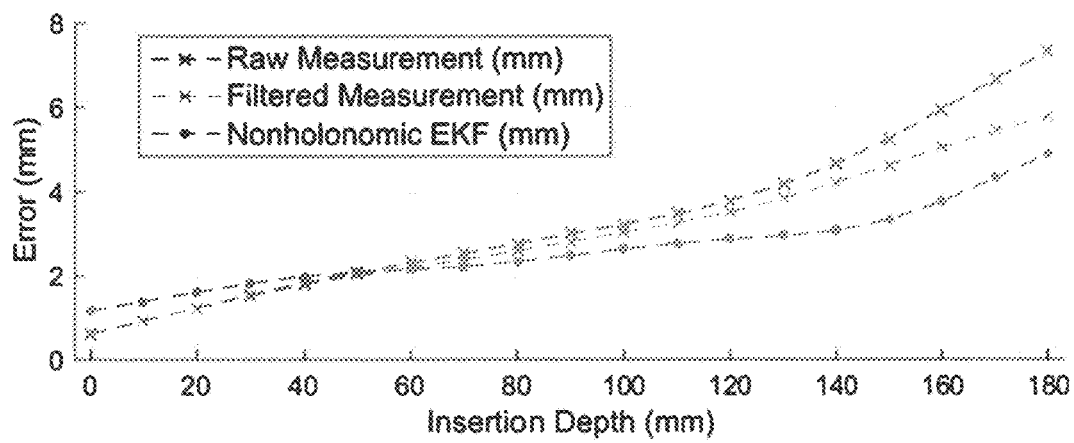
FIG. 9B is a plot showing a comparison of position estimation errors at various insertion depths for ten catheter paths (data points were down-sampled for graphic clarity).

Unfiltered tracking data led to path reconstructions characterized by a mean error of 3.7 mm over the ten paths. As illustrated in FIG. 9B, the greater the insertion depth, the more inaccurate the reconstruction. Raw measurements led to a noisy reconstruction of the paths with an associated mean standard deviation of 1.8 mm.

Reconstruction using the Manufacturer's Filters

Manufacturer's filters efficiently increased the tracking accuracy, leading to an improved reconstruction of the catheter paths with an associated mean error of 3.3 mm. As detailed in Table 3, the standard deviation of the reconstruction error was also reduced to 1.6 mm.

Reconstruction using the EKE method

The EKF with the nonholonomic motion model further reduced the mean error to 2.7 mm, with an improved 95% confidence interval (CI) of 4.5 mm. With a standard deviation of the error of 1.1 mm, random noise (jitter) was efficiently reduced by this approach as well. As shown in FIGS. 9A and 9B, the filter significantly improved the accuracy of path reconstructions compared to the manufacturer's filter, with a p-value of $p<0.01$ in a two-sample t-test.

In the analysis of the tracking error distribution, higher reconstruction errors were observed when the sensor was located further away from the transmitter. The filter was able to reduce these measurement errors, where the estimated error at the tip of the catheter (farthest point from the transmitter) was approximately 1 mm lower than the one reported by the standard manufacturer's filter. To achieve enhanced reconstructions, the transmitter should be placed centrally with respect to the complete insertion site, and unnecessary metallic and magnetic field distorting objects should be removed.

Based on the above results, the experimental setup was optimized and perthrmance was evaluated a second time. The results, based on ten distinct path reconstructions at manual sensor retraction speeds approximating 15 mm*s$^{-1}$, are shown in Table 4. Compared to the raw measurements, the nonholonomic EKF approach significantly improved path reconstruction accuracies by 46% and precisions by 53%. The mean error was reduced from 3.5 mm to 1.9 mm, and the associated 95% CI was decreased from 6.2 mm to 3.1 mm. Compared to the manufacturer's filters, the nonholonomic EKF filter also significantly improved path reconstruction accuracies by 21% and precisions by 20%. Furthermore, the repeatabilities in reconstruction accuracy were assessed to be approximately 0.1 mm using the raw measurements, the manufacturer's filters approach, and the nonholonomic EKF technique.

TABLE 4

Path reconstruction results of ten catheters (values in mm).

| | Raw measurements | Manufacturer's filters | Nonholonomic EKF |
|---|---|---|---|
| Accuracy | 3.5 | 2.4 | 1.9 |
| Precision | 1.7 | 1.0 | 0.8 |
| 95% CI | 6.2 | 3.9 | 3.1 |
| Max Error | 13.5 | 8.0 | 5.9 |

Figure 10:
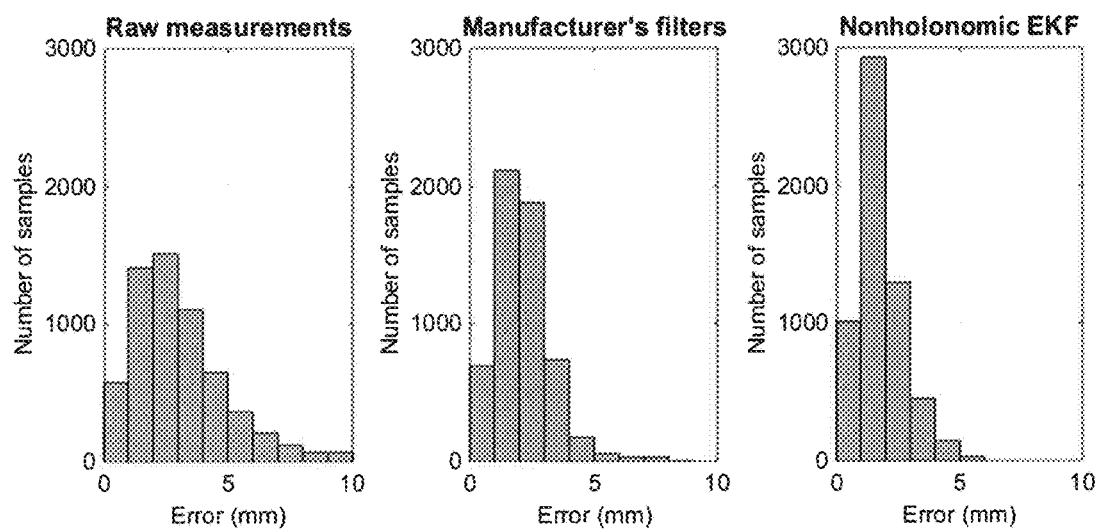
FIG. 10 shows plots of frequency of sample reconstruction errors of ten catheter paths using raw measurement data (left), manufacturer's filter (center), and a nonholonomic EKF filter (right) according to one embodiment (for clarity, raw measurement errors greater than 10 mm are annexed to those ranging from 9 to 10 mm).

The histogram of FIG. 10 shows the distribution of all the paths sample reconstruction errors. Sample reconstruction errors using the nonholonomic EKF technique mainly fell between 1 and 3 mm. Moreover, catheter path reconstructions were achieved with accuracy errors under 6 mm, as reported in Table 4; in comparison, reconstructions of paths using both the raw measurements and the measurements using the manufacturer's filters resulted in sample errors exceeding 8 mm.

Table 5 lists the path reconstruction accuracies as a function of the mean distance of the path relative to the transmitter. Results of path reconstructions as a function of sensor retraction velocity and path curvature (i.e., path IDs 8, 9, 10) are also shown in Table 5. In path IDs 8, 9, 10 (with minimum, maximum, and moderate curvatures), several sensor speeds were used to assess the impacts of sensor retraction speed and path curvature on the nonholonomic EKF filter performance. Reported low speeds ranged between 7.4 and 9.8 mm*s$^{-1}$, medium speeds between 14.1 and 20.3 mm*s$^{-1}$, and high speeds between 23.6 and 32.1 mm*s$^{-1}$. The performance of the path reconstructions did not follow an apparent trend When varying the path curvature and sensor velocity. Instead, when the sensor was retracted from a path farther from the reference (field) transmitter (i.e., path IDs 1, 5, 7), there was a clinically significant decrease in reconstruction accuracy.

TABLE 5

Path reconstruction RMS accuracies, as a function of the mean distance from the field transmitter (FT) and mean path curvature (values are mean ± standard deviation).

| Path ID | Distance from FT (mm) | Curvature ($m^{-1}$) | Sensor velocity | Raw measurement accuracy (mm) | Manufacturer's filters accuracy (mm) | Nonholonomic EKF accuracy (mm) |
|---|---|---|---|---|---|---|
| 1 | 259 ± 23 | 4.5 ± 2.9 | Medium | 2.9 ± 1.3 | 2.2 ± 0.9 | 1.6 ± 0.7 |
| 2 | 260 ± 44 | 3.8 ± 2.5 | Medium | 3.5 ± 1.9 | 2.2 ± 0.8 | 1.7 ± 0.6 |
| 3 | 265 ± 13 | 1.9 ± 1.6 | Medium | 2.9 ± 1.4 | 2.2 ± 0.9 | 2.0 ± 0.8 |
| 4 | 267 ± 44 | 3.8 ± 2.5 | Medium | 3.7 ± 2.0 | 2.3 ± 0.9 | 1.7 ± 0.7 |
| 5 | 274 ± 26 | 6.4 ± 5.7 | Medium | 3.6 ± 1.8 | 2.6 ± 1.2 | 2.2 ± 1.0 |
| 6 | 281 ± 19 | 3.7 ± 3.1 | Medium | 4.4 ± 2.1 | 2.5 ± 1.0 | 2.7 ± 1.3 |
| 7 | 294 ± 19 | 3.9 ± 1.8 | Medium | 4.9 ± 2.4 | 3.8 ± 1.9 | 2.7 ± 1.3 |
| 8 | 234 ± 24 | 0.0 ± 0.0 | Low | 2.3 ± 1.0 | 1.7 ± 0.7 | 1.6 ± 0.7 |
| 8 | 234 ± 24 | 0.0 ± 0.0 | Medium | 2.3 ± 1.0 | 1.6 ± 0.7 | 1.6 ± 0.7 |
| 8 | 234 ± 24 | 0.0 ± 0.0 | Medium | 2.3 ± 1.0 | 1.8 ± 0.6 | 1.7 ± 0.6 |
| 9 | 260 ± 26 | 6.6 ± 6.1 | Low | 3.3 ± 1.6 | 2.4 ± 1.0 | 2.0 ± 0.9 |
| 9 | 260 ± 26 | 6.6 ± 6.1 | Medium | 3.2 ± 1.5 | 2.4 ± 1.0 | 1.5 ± 0.6 |
| 9 | 260 ± 26 | 6.6 ± 6.1 | High | 3.6 ± 1.6 | 2.5 ± 1.2 | 2.4 ± 0.9 |
| 10 | 267 ± 13 | 4.7 ± 3.9 | Low | 3.1 ± 1.5 | 2.1 ± 0.8 | 1.9 ± 0.7 |
| 10 | 267 ± 13 | 4.7 ± 3.9 | Medium | 3.1 ± 1.5 | 2.1 ± 0.8 | 1.8 ± 0.6 |
| 10 | 267 ± 13 | 4.7 ± 3.9 | High | 3.2 ± 1.5 | 2.2 ± 1.0 | 1.7 ± 0.7 |

Discussion

The results confirm that the nonholonomic EKF filter significantly enhanced EM measurement accuracy compared to the general filters provided by manufacturer. The nonholonomic EKF showed to be robust to both sensor retraction velocities and path curvatures; in fact, path reconstruction accuracy did not follow a clinically significant trend when the path curvature and sensor velocity varied. A spatial accuracy tolerance of 3 mm for HDR prostate brachytherapy has been recommended. Even for sensor velocities as high as 32.1 mm*s$^{-1}$ and curvatures as high as 6.6 m$^{-1}$, reconstruction performance using the advanced filter was consistent with this clinical need.

EM field distortions from the HDR prostate brachytherapy setup had a lower impact on the tracking accuracy than expected. A study was also performed in a research environment, where raw measurement errors were 3.7 mm, measurement errors using the manufacturer's filters were 3.3 mm, and measurement errors using the nonholonomic EKE filter were 2.7 mm Compared with these figures, measurement errors in the brachytherapy suite were reduced to 3.5 mm (or 5%), 2.4 mm (or 27%), and 1.9 mm (or 30%), respectively. In the brachytherapy suite, the field transmitter was installed closer to the complete target volume, which may have resulted in the increase of tracking accuracy. It is therefore favorable to maintain the EM transmitter at an optimum position relative to the clinical target area in order to enhance EM measurements.

Conventional catheter identifications are time-consuming and challenging. EM tracking assistance can substantially shorten this procedure time. In fact, a typical retraction speed of 15 mm*s$^{-1}$ was observed in this example; with an insertion depth of 150 mm, insertion and retraction of the sensor in each catheter path would span 20 seconds. Moreover, the proposed filter was approximately executed at the rate of 20 Hz on a single Intel Core 4.00 GHz CPU, which is well beyond the EM sampling rate of 60 Hz, and would not extend the treatment planning time. In turn, EM tracking may abbreviate the reconstruction process time to a couple of minutes.

Figure 11:
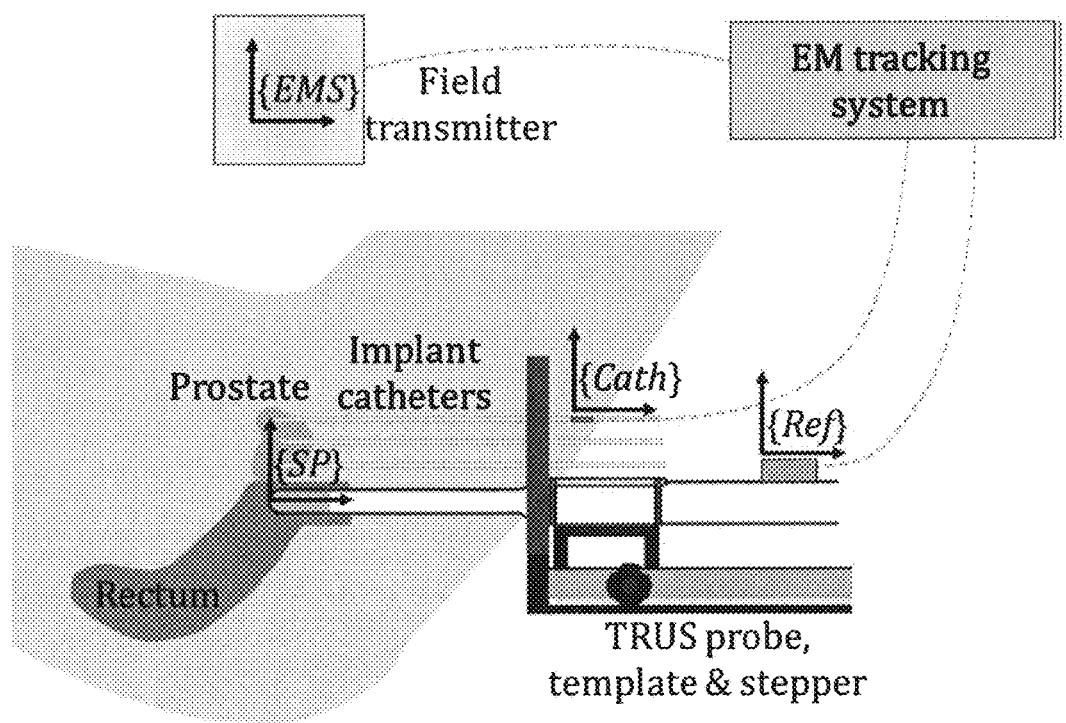
FIG. 11 is a schematic diagram showing an example of a clinical setup for prostate HDR brachytherapy, including a TRUS probe and stepper, and the EM tracking system's reference coordinate frame $\{EMS\}$ attached to the field transmitter.

For EM assistance for HDR prostate brachytherapy, a general workflow may be implemented clinically as described below and in FIG. 11. Here, the catheters and the TRUS probe are tracked by EM sensors. {Cath} is the coordinate frame attached to the sensor placed inside the catheter (a miniature EM sensor is threaded into the catheter in order to observe its path), and {Ref} is the coordinate frame attached to the EM sensor mounted on the TRUS probe. The reference frame for TRUS image scan plane is denoted {SP}. To reconstruct a catheter path with respect to the prostate volume, the catheter path and TRUS images of the prostate are both represented in the same reference coordinate frame {EMS}. Furthermore, the TRUS probe may be tracked using a large EM sensor, and the TRUS image scan planes {SP} may be registered to the TRUS probe {Ref} through well-established calibration methods. Therefore, the catheter path can be represented with respect to the TRUS images using the following equation:

$$_{SP}T^{Cath} = {}_{SP}T^{Ref} \cdot ({}_{EMS}T^{Ref})^{-1} \cdot {}_{EMS}T^{Cath} \quad (34)$$

The tracking system provides the transformations $_{EMS}T^{Ref}$, from {Ref} to {EMS}, $_{EMS}T^{Cath}$, from the catheter sensor {Cath} to {EMS}. The calibration step establishes the transformation $_{SP}T^{Ref}$, from {Ref} to {SP}. Finally, the DICOM (digital imaging and communication in medicine) TRUS images and the catheter path reconstructions expressed as a structure set may be exported (e.g., to Oncentra; www.elekta.com/brachytherapy/oncentra-brachytreatment-planning.html) for treatment planning.

The results presented in this paper show that catheter path reconstruction accuracies are in line with the clinical need. Nonetheless, TRUS images and path reconstructions should be spatially calibrated. The inherent errors of TRUS probe tracking and calibration procedures are expected to decrease the reported path reconstruction accuracies relative to the patient's organs. In the clinical setup shown in FIG. 11, only two EM sensors {Cath} and {Ref} are employed, and two sensor ports remain available on a standard Ascension tracker. To overcome TRUS probe tracking errors induced by the presence of metallic objects surrounding the setup, redundant tracking of the probe may further increase the HDR path reconstruction accuracy with respect to the TRUS images. Such redundant measurements may be integrated using an algorithm that dynamically detects and compensates for the EM field distortions in order to improve the tracking performance of the TRUS probe. Therefore, complete EM assistance for HDR prostrate brachytherapy may be achieved by a combination of EM tracking of the catheter paths using a specialized nonholonomic EKF filter and EM tracking of the TRUS probe, through a simultaneous localization and field distortion mapping algorithm.

EXAMPLE 4

Robust Electromagnetic Tracking of Ultrasound Probes in High-dose-rate Brachytherapy High-dose-rate (HDR) brachytherapy has become a widely accepted treatment for cancers as it offers excellent tumor control while sparing normal tissue. An HDR brachytherapy treatment involves implanting catheters inside the tissue; treatment planning is then generated, which consists of determining the catheter positions with respect to clinical target volume, and optimizing the dwell times and positions within each catheter. Finally, a radioactive source is inserted into the catheter, and is withdrawn by steps of a few millimeters to deliver the dose prescribed during the treatment planning. Therefore, it is critical to accurately reconstruct catheter paths with respect to the target tissue. Failure to do so may result in under-treating the tumor, and over-treating surrounding normal tissue.

Electromagmetic (EM) tracking of an ultrasound (US) probe can increase the accuracy, objectivity, and speed of planning a HDR brachytherapy treatment. However, various instruments—including the US probe—may introduce dynamic distortions to the EM field, and compromise the EM measurements. Basic filtering methods, such as those provided by manufacturers, are usually inefficient as they do not allow for field distortion compensation.

In this example the simultaneous localization and mapping (SLAM) algorithm is used to track a transrectal ultrasound (TRUS) probe during prostate brachytherapy and dynamically detect, map, and correct the EM field distortions. Redundant EM sensors are attached to the TRUS probe in order to assess, map, and compensate for the EM field distortions. Combining the motion model of the tracked probe, the redundant EM observations, and the relative location of the sensors, the SLAM algorithm provides robust and accurate estimations of the location of the tracked instrument and the field distortions map. See, e.g., FIG. 1C, which shows inputs including the motion model of the TRUS probe, the EM sensor measurements, the measurement uncertainty, and spatial parameters representing the relative locations of the EM sensors. This method has been successfully employed in various applications and recently introduced for EM instrument tracking in computer assisted interventions.

Materials and Methods

The performance of EM tracking a TRUS probe can be significantly improved through an extended Kalman filter (EKF) based SLAM algorithm and at least one redundant EM sensor. Two steps are then required: first, quantifying the setup parameters, and second, performing the simultaneous tracking and calibration processes.

Setup Parameter Quantification

Inputs of the SLAM algorithm include the spatial configuration between the EM sensors, as well as their measurement uncertainties. These parameters were assessed pre-operatively.

Figure 12:
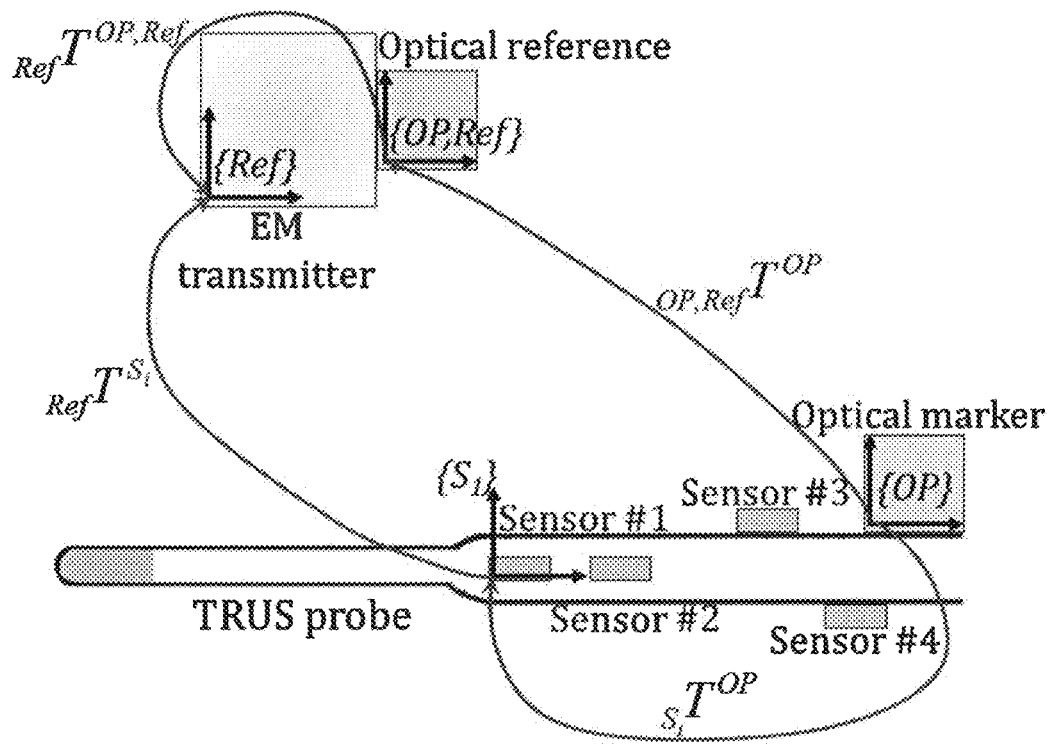
FIG. 12 is a schematic diagram showing an experimental setup, with relevant coordinate systems and transformations, for a TRUS probe tracking embodiment.

Spatial parameters As shown in FIG. 12, four EM sensors were mounted on the TRUS probe in order to track an arbitrary target frame; sensors measurements are, by default, expressed in the coordinate frame {Ref} of the field transmitter. Furthermore, the probe was tracked by a NDI Spectra optical system (Waterloo, Ontario, Canada) to provide a ground truth for the experiments. As illustrated in FIG. 12, the transformations $_{OP,Ref}T^{OP}$ from the optical marker's frame {OP} to an optical tracker's reference frame {OP,Ref} were provided by the optical tracking system. The spatial parameters identify the relative transformations between each of the four EM sensor frames $\{S_i\}$, with i=1, 2, 3, 4, and the target frame. For convenience, the target frame was attached to that of the optical marker's coordinate frame {OP}. The unknown transformations $_{Si}T^{OP}$ from the target {OP} to each sensor frame $\{S_i\}$, and $_{Ref}T^{OP,Ref}$ from {OP, Ref} to {Ref}, as shown in FIG. 12, were computed using a well-established concurrent hand-eye calibration. In turn, the establishment of spatial parameters $_{Si}T^{OP}$ enabled computation of the target's pose via the EM measurements as:

$$_{Ref}T^{OP} = {}_{Ref}T^{Si} \cdot {}_{Si}T^{OP} \tag{35}$$

Finally, the transformation $_{Ref}T^{OP,Ref}$ enabled verification of the target's pose via the ground truth measurements as:

$$_{Ref}T^{OP} = {}_{Ref}T^{OP,Ref} \cdot {}_{OP,Ref}T^{OP} \tag{36}$$

For convenience in the notations, all EM measurements are expressed in {Ref}.

Measurement uncertainty parameters The uncertainty associated with each sensory observation is provided to the SLAM algorithm. An automated uncertainty assessment was conducted to quantify the measurement uncertainty of an Ascension model 800 EM sensor. Two robotic arms moved the sensor throughout the EM tracking volume in a research environment with minimum field distortions. The ground truth was provided by the NDI Spectra with submillimetric accuracy. A robust multilinear regression method was employed in order to recover the measurement uncertainty parameters.

Motion Model

The SLAM algorithm uses the motion model of the TRUS probe in the EKF, in addition to the EM measurements Z, and measurement uncertainty and spatial parameters defined above.

The motion model describes the transition between each state X. At a discrete time step k, the state $X_k$ was defined as:

$$X_k = [p_k \; q_k \; \dot{p}_k \; w_k]^T \tag{37}$$

where p denotes the position vector, q the orientation (quaternion), $\dot{p}$ the linear velocity, and w the angular velocity. A general motion model was employed. In turn, $$\begin{bmatrix} p_k \\ q_k \\ \dot{p}_k \\ w_k \end{bmatrix} = \begin{bmatrix} p_{k-1} + dt \cdot \dot{p}_{k-1} \\ \exp(dt \cdot \phi(w_{k-1})) \cdot q_{k-1} \\ \dot{p}_{k-1} \\ w_{k-1} \end{bmatrix} \tag{38}$$

with $\phi$ defined by:

$$\phi(w) = 1/2 \begin{bmatrix} w \times & w \\ -w^T & 0 \end{bmatrix} \tag{39}$$

and the operator × is the vector cross product expressed as a skew-symmetric matrix.

Experimental Validation

An Ascension (Burlington, Vt., U.S.A.) trakSTAR EM tracking system was employed. Four EM sensors (model 800) were attached to the TRUS probe. Sensor mounting configuration is schematically illustrated in FIG. 12, where sensor #2, #3, and #4 were placed approximately 25 mm, 56 mm, and 71 mm, respectively, away from sensor #1. Data from this DC-based tracking system was collected using the application "Cubes", provided by the manufacturer, at a sampling rate of 60 Hz. Furthermore, the probe was tracked by the NDI Spectra in order to provide a ground truth for the experiments. This optical system was controlled using the NDI Toolbox software, and data was also collected at a sampling rate of 60 Hz. A spatial and a temporal calibration between the EM system and the optical system were performed. Additionally, a constant lag estimation (Sadjadi, H, et al, "Simultaneous Localization and Calibration for Electromagnetic Tracking Systems," The International Journal of Medical Robotics and Computer Assisted Surgery (IJMR-CAS), 2015) was also taken into consideration in order to synchronize both tracking systems.

Experiments were conducted in an HDR brachytherapy suite where significant field distorting objects surrounded the experimental setup, including the stepper and the probe itself. In fact, to simulate a TRUS imaging procedure, the tracked probe was rigidly maintained by a stepper mounted on a metallic stabilizer. In order to image the prostate using either sequential axial sections (from the base to apex) or a sagittal volume-based technique (from right to left), the probe was translated along its longitudinal axis and rotated around the same longitudinal axis. In addition, data was collected during freehand motions of the probe, consisting of simultaneous translation and rotation displacements. Probe motions were reproduced six times in order to evaluate the repeatability in the accuracy of the sensors measurements and the SLAM estimations.

Performance Analysis

The SLAM method was compared against the direct EM measurements using the default filtering techniques provided by the manufacturer, namely the AC wide notch and the DC adaptive filter. The performance of the SLAM method was further investigated as a function of the amount of redundant sensory measurements.

Position tracking accuracy was determined by computing the Euclidean distance between each position measurement and the corresponding ground truth. Similarly, orientation tracking accuracy was calculated by computing the difference of angle between each orientation measurement and its corresponding gound truth. The RMS measurement accuracies, 95% confidence intervals (CI), as well as the RMS precisions were computed.

Results

The tracking performance was assessed using four model 800 sensors. Using the manufacturer's filters, tracking of freehand motions had RMS accuracies ranging from 2.0 to 2.8 mm and 1.4 to 1.6 degrees. Tracking of the TRUS probe using the SLAM technique was associated with RMS tracking errors of 1.5 mm and 1.3 degrees; in turn, SLAM enabled an increase of the estimation accuracy up to 46.4%.

Table 6 further lists tracking results as a function of TRUS probe translation and rotation. Position measurement accuracies were not significantly impacted by the translation and rotation of the TRUS probe. Conversely, orientation measurements were considerably improved during translation motions of the TRUS probe, in contrast to rotation and freehand motions. Finally, the repeatabilities in tracking accuracies ranged from 0.2 to 0.7 mm and 0.0 to 0.3 degrees using the manufacturer's filters and the SLAM technique.

Figure 13:
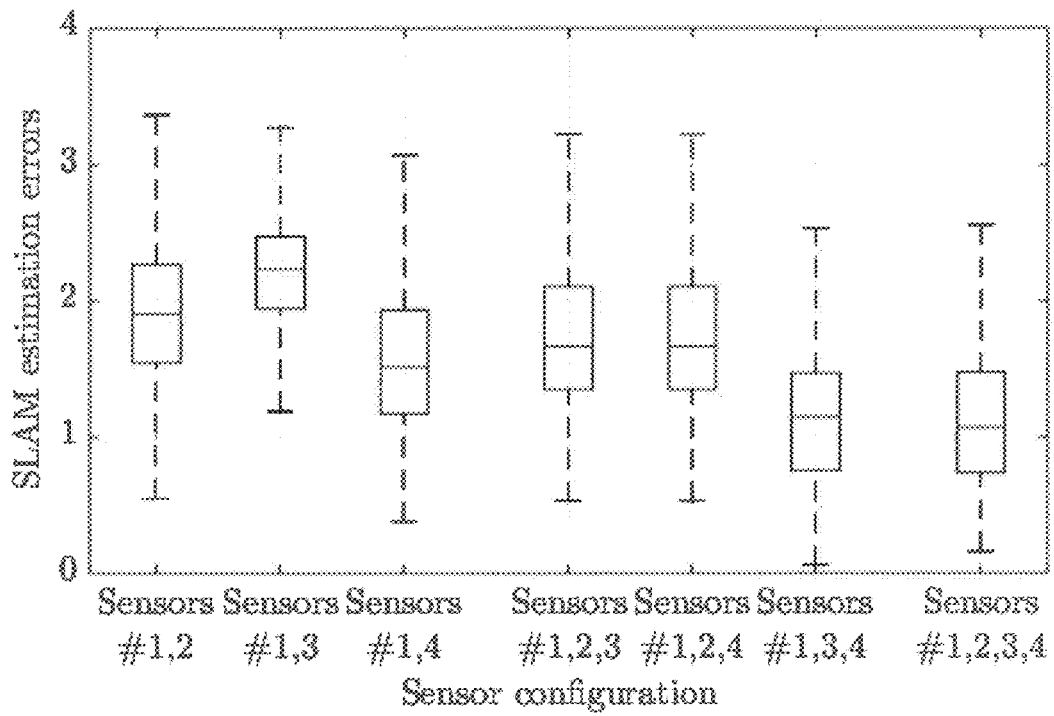
FIG. 13 is a plot showing errors (median, 25th and 75th percentiles, and extreme non-outlying errors) in SLAM estimations of TRUS probe position during a freehand motion, as a function of the number of EM sensors, and their mounting configurations relative to a sensor.

The number of redundant measurements influenced the SLAM estimation performance of the position measurements. Indeed, the SLAM performance improved as the number of sensor observations increased. FIG. 13 depicts this phenomenon; as can be seen, the errors in the SLAM estimations generally decreased as more sensor measurements became available.

TABLE 6

EM TRUS probe tracking results (values in mm and degrees)

|  |  | Sensor #1 | | Sensor #2 | | Sensor #3 | | Sensor #4 | | SLAM filter | |
| --- | --- | --- | --- | --- | --- | --- | --- | --- | --- | --- | --- |
|  |  | Position | Orientation | Position | Orientation | Position | Orientation | Position | Orientation | Position | Orientation |
| Freehand | Accuracy RMS | 2.2 | 1.4 | 2.0 | 1.4 | 2.8 | 1.6 | 2.8 | 1.4 | 1.5 | 1.3 |
|  | Precision | 0.8 | 1.1 | 0.7 | 1.1 | 0.7 | 1.1 | 0.7 | 1.1 | 0.9 | 1.2 |
|  | 95% CI | 3.2 | 3.1 | 2.9 | 3.0 | 3.9 | 3.1 | 3.7 | 3.0 | 2.8 | 3.0 |
| Translation | Accuracy RMS | 2.3 | 0.3 | 1.9 | 0.5 | 2.3 | 0.8 | 2.7 | 0.6 | 1.3 | 0.1 |
|  | Precision | 0.5 | 0.1 | 0.4 | 0.0 | 0.3 | 0.0 | 0.3 | 0.0 | 0.5 | 0.0 |
|  | 95% CI | 3.3 | 0.4 | 2.6 | 0.6 | 2.7 | 0.8 | 3.2 | 0.7 | 2.0 | 0.2 |
| Rotation | Accuracy RMS | 2.0 | 1.5 | 2.0 | 1.5 | 2.5 | 1.7 | 2.0 | 1.6 | 1.4 | 1.5 |
|  | Precision | 0.4 | 0.8 | 0.6 | 0.7 | 0.4 | 0.7 | 0.7 | 0.7 | 0.6 | 0.8 |
|  | 95% CI | 2.5 | 2.5 | 2.9 | 2.4 | 3.2 | 2.7 | 4.1 | 2.3 | 2.3 | 2.5 |

The effect of sensor configuration on SLAM performance is further characterized in FIG. 13. Although estimation accuracies generally increased with the number of redundant sensors, the mounting configuration of the sensors was also observed to significantly impact the SLAM efficiency to correctly track and compensate for the field distortions. In fact, higher estimation accuracies were observed when the sensors were located farther from each other (sensors #1, 4). Moreover, tracking the target with three sensors poorly mounted (sensors #1, 2, 3) was more erroneous than using two sensors optimally placed on the TRUS probe. Optimum configurations were observed when the sensors were placed in a non-collinear way (sensors #1, 3, 4, as well as sensors #1, 2, 3, 4).

Discussion

The SLAM method was shown to significantly improve TRUS tracking accuracy and precision. As more sensory observations were made, the higher the tracking performance. In turn, mounting multiple redundant sensors helps SLAM to accurately estimate the target location and create the field distortion maps. Nevertheless, an optimized sensor configuration around the probe is also a key factor to the SLAM performance. Indeed, a superior configuration of fewer sensors was sometimes observed to be more valuable for accurate TRUS tracking than employing a higher number of sensors with a poor configuration. Optimum configurations were observed when the sensors were placed in a non-collinear way.

SLAM heavily relies on EM field distortion detection and compensation to properly estimate the tracking measurements. Compared with the manufacturer's filtering techniques which do not include any compensation for the field distortions, the SLAM approach increased TRUS probe tracking accuracy up to 46.4% during freehand motions of the TRUS probe. The results suggest that the advanced approach integrating SLAM and EM tracking provides a viable alternative when optical tracking is not possible.

EM tracking assistance in HDR, prostate brachytherapy relies on concurrent tracking of the TRUS probe and catheter paths. In order to achieve this goal, a spatial tolerance of 3 mm was suggested. EM-based path reconstruction accuracies were shown to be 1.9 mm. In this work, EM tracking of the TRUS probe was experimentally validated for both the sequential axial sections and the sagittal volume-based imaging techniques. Results showed that SLAM effectively reduced tracking errors to 1.3 mm and 0.1 degrees for the sequential axial sections imaging method, as well as 1.4 mm and 1.5 degrees for the sagittal volume-based technique. Accordingly, the application of EM tracking assistance in HDR prostate brachytherapy procedures is further advanced using the SLAM method. The results suggest that the method would make applicable complementary EM tracking to ultrasound-guided HDR brachytherapy, resulting in both a dramatic shortening of the treatment planning time and an enhanced treatment delivery.

INCORPORATION BY REFERENCE

All cited references and publications are incorporated herein by reference in their entirety.

Equivalents

While the invention has been described with respect to illustrative embodiments thereof, it will be understood that various changes may be made to the embodiments without departing from the scope of the invention. Accordingly, the described embodiments are to be considered merely exemplary and the invention is not to be limited thereby.

The invention claimed is:

1. Apparatus for electromagnetic (EM) tracking or localization in a workspace, comprising:
   one or more EM transmitter and two or more EM sensors, wherein one EM sensor is a redundant EM sensor that is adapted to be mounted on an instrument during a procedure such that the redundant sensor moves with the instrument during, the procedure;
   a processor that receives signals from the two or more EM sensors, and
   (i) estimates uncertainty associated with each EM sensor measurement,
   (ii) determines an indication of relative locations of the two or more EM sensors with respect to the instrument, and
   (iii) generates a field distortion map of the workspace of procedure;
   wherein a field distortion estimator uses currently-available information of the field distortion map and estimates field distortion for the workspace, including a location of the instrument;
   wherein information from the redundant sensor is used with the field distortion estimator to produce an output that compensates for field distortion at a location of the instrument in real time during the procedure; and
   wherein a transient analyzer continuously observes variations in the field distortion map over time in order to differentiate regions with continuous changes from regions with constant field distortion, and provides feedback to the field distortion estimator, including predicting how the field distortion map is expected to change;
   wherein the estimates of uncertainty associated with each EM sensor measurements, the relative locations of the two or more EM sensors, and the output from the field distortion estimator are used by a probabilistic simultaneous localization and mapping (SLAM) algorithm that simultaneously estimates a location and pose of the workspace, and updates the field distortion map, in real time;
   the apparatus further comprising an output device that outputs a location and pose of the instrument in in the workspace during the procedure;
   wherein the location and pose of the instrument is substantially corrected for EM field distortion in real time.

2. The apparatus of claim 1, wherein the field distortion estimator estimates field distortion based on interpolating, or adjusting model parameters of the field distortion map.

3. The apparatus of claim 1, wherein the SLAM algorithm uses Bayesian inference for estimation and is implemented by one or more of a Kalman filter, a particle filter, and non-linear least squares.

4. A method for electromagnetic (EM) tracking or localization in a workspace, comprising:
   providing one or more EM transmitter and two or more EM sensors, wherein one EM sensor is a redundant EM sensor that is adapted to be mounted on an instrument during a procedure such that the redundant sensor moves with the instrument during the procedure;
   receiving signals from the two or more EM sensors, and using a processor to
   (i) estimate uncertainty associated with each EM sensor measurement,
   (ii) determine an indication of relative locations of the two or more EM sensors with respect to the instrument, and
   iii) generate a field distortion map of the workspace of the procedure;
   the method further comprising:
   implementing a field distortion estimator that uses currently-available information of the field distortion map to estimate field distortion for the workspace, including a location of the instrument;
   using information from the redundant sensor with the field distortion estimator to produce an output that compensates for field distortion at a location of the instrument in real time during the procedure;
   continuously observing variations in the field distortion map over time to differentiate regions with continuous changes from regions with constant field distortion, and providing feedback to the field distortion estimator, including predicting how the field distortion map is expected to change;
   wherein the estimates of uncertainty associated with each EM sensor measurements, the relative locations of the two or more EM sensors, and the output from the field distortion estimator are used by a probabilistic simultaneous localization and mapping (SLAM) algorithm that simultaneously estimates a location and pose of the instrument in the workspace, and updates the field distortion map, in real time; and outputting, a location and pose of the instrument in the workspace during the procedure;

wherein the location and pose of the instrument is substantially corrected for EM field distortion in real time.

5. The method of claim 4, wherein the field distortion estimator estimates field distortion based on interpolating, or adjusting model parameters of the field distortion map.

6. The method of claim 4, wherein the SLAM algorithm uses Bayesian inference for estimation and is implemented by one or more of a Kalman filter, a particle filter, and non-linear least squares.

7. Programmed media for use with a computer and with EM sensor data, wherein the EM sensors comprise one or more EM transmitter and two or more EM sensors, wherein one EM sensor is a redundant EM sensor that is adapted to be mounted on an instrument during a procedure such that the redundant sensor moves with the instrument during the procedure, the programmed media comprising a computer program stored on non-transitory storage media compatible with the computer, the computer program containing instructions to direct the computer to perform one or more of;

(i) estimate uncertainty associated with each EM sensor measurement, (ii) determine an indication of relative locations of the two or more EM sensors with respect to the instrument, and (iii) generate a field distortion map of the workspace of the procedure;

implement a field distortion estimator that uses currently-available information of the field distortion map to estimate field distortion for the workspace, including a location of the instrument;

use information from the redundant sensor with the field distortion estimator to produce an output that compensates for field distortion at a location of the instrument in real time during the procedure;

continuously observe variation in the field distortion map over time to differentiate regions with continuous changes from regions with constant field distortion, and provide feedback to the field distortion estimator, including predicting how the field distortion map is expected to change;

wherein the estimates of uncertainty associated with each EM sensor measurements, the relative locations of the two or more EM sensors, and the output from the field distortion estimator are used by a probabilistic simultaneous localization and mapping (SLAM) algorithm that simultaneously estimates a location and pose of the instrument in the workspace, and updates the field distortion map, in real time; and output a location and pose of the instrument in the workspace during the procedure;

wherein the location and pose of the instrument is substantially corrected for EM field distortion in real time.

8. The apparatus of claim 1, wherein measurements are combined or filtered with kinematic motion models and/or dynamic motion models, including but not limited to weighted averages, or a stochastic sensor fusion technique.

9. The apparatus of claim 8, including a Kalman filter.

10. The apparatus of claim 1, wherein the instrument is an object or feature being tracked or localized; wherein the instrument comprises a gaming device, a tool, a surgical tool, an animal, a human, or a feature in a simulator.

11. The method of claim 4, wherein the instrument is an object or feature being tracked or localized; wherein the instrument comprises a gaming device, a tool, a surgical tool, an animal, a human, or a feature in a simulator.

12. The method of claim 7, wherein the instrument is an object or feature being tracked or localized; wherein the instrument comprises a gaming device, a tool, a surgical tool, an animal, a human, or a feature in a simulator.

13. The apparatus of claim 1, wherein the instrument is a catheter, a needle, a cutting tool, a cautery tool, or a guide-wire.

* * * * *